US007981460B2

(12) United States Patent
Amino et al.

(10) Patent No.: US 7,981,460 B2
(45) Date of Patent: Jul. 19, 2011

(54) SUBSTITUTED BENZYL ESTER DERIVATIVE AND USE THEREOF

(75) Inventors: Yusuke Amino, Kawasaki (JP); Yoshinobu Takino, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/345,249

(22) Filed: Dec. 29, 2008

(65) Prior Publication Data

US 2009/0203774 A1 Aug. 13, 2009

Related U.S. Application Data

(63) Continuation of application No. PCT/JP2007/063170, filed on Jun. 29, 2007.

(30) Foreign Application Priority Data

Jun. 29, 2006 (JP) ................................. 2006/180433

(51) Int. Cl.
*A61K 31/235* (2006.01)
*A23L 1/30* (2006.01)
*C07D 323/02* (2006.01)
*C07D 317/44* (2006.01)

(52) U.S. Cl. ........ 426/648; 514/544; 549/434; 549/445; 549/447

(58) Field of Classification Search ................. 554/229; 514/544, 885; 426/648; 549/445, 434, 447
See application file for complete search history.

(56) References Cited

U.S. PATENT DOCUMENTS

| 6,333,421 | B1 | 12/2001 | Yazawa et al. | |
|---|---|---|---|---|
| 7,576,125 | B2 * | 8/2009 | Ishida et al. | ................. 514/464 |
| 2005/0239883 | A1 | 10/2005 | Tani et al. | |
| 2007/0020738 | A1 | 1/2007 | Amino et al. | |

FOREIGN PATENT DOCUMENTS

| JP | 61-269154 | 11/1986 |
|---|---|---|
| JP | 2001-240986 | 9/2001 |
| JP | 3345744 | 9/2002 |
| WO | WO 2004/100942 A1 | 11/2004 |
| WO | WO 2005/099682 A1 | 10/2005 |

OTHER PUBLICATIONS

Wilkinson et al, some Structural Requirements of Methylenedioxyphenyl derivatives a synnergists of Carbamate Insecticides, J. of Agriculture & food chemistry, 1966, 14(1), p. 73-79.*
Henin et al, Photodeconjugaison enantioselelctive D'Esters Et De Lactone conjugues En Presence D'ephedrine, 1989, Tetrahedron, 45(19), p. 6171-6186.*
Kang et al, Isonitrile- nitrile rearrangement promoted by samarium (II) iodide, 1997, Chemical Communications, 9, p. 821-822.*
U.S. Appl. No. 12/237,142, filed Sep. 24, 2008, Amino, et al.
M. E. Neubert, et al., "The effect of Carbonyl Containing Terminal Chains on Mesomorphic Properties in 4,4'-Disubstituted Phenylbenzoates and Phenylthiobenzoates. 5. Phenylbenzoates Containing a $(CH_2)_n$ $O_2$ CR' Group (n= 1,2) on the Phenolic End", Mol. Cryst. Liq. Cryst., vol. 206, 1991, pp. 103-116.
A. Torres de Pinedo, et al., "Efficient lipase-catalyzed synthesis of new lipid antioxidants based on a catechol structure", Tetrahedron, vol. 61, 2005, pp. 7654-7660.
Novel Capsaicinoid-like Substances, Capsiate and Dihydrocapsiate, from the fruits of a Nonpungent Cultivar, CH-19 Sweet, of Pepper (*Capsicum annuum* L.), Journal of Agricultural and Food Chemistry, Rapid Communications, vol. 46, No. 5, May 1998, pp. 1695-1697.
Kouzou Sutoh, et al., "Stability of Capsinoid in Varios Solvents", J. Agric. Food Chem., vol. 49, No. 8, 2001, pp. 4026-4030.
S. I. Gertler, et al., "Syntheses of Compounds with the Methylenedioxyphenyl Group", J. Org. Chem., vol. 24, Mar. 1959, pp. 327-329.
Angewandte Chemie, vol. 94, No. 10, 1982, p. 785.
Antonio Macho, et al., "Involvement of Reactive Oxygen Species in Capsaicinoid-induced Apoptosis in Transformed Cells", Free Radical Research, vol. 37, No. 6, 2003, pp. 611-619.
U.S. Appl. No. 12/711,629, filed Feb. 24, 2010, Amino, et al.

* cited by examiner

Primary Examiner — Victor Oh
(74) Attorney, Agent, or Firm — Oblon, Spivak, McClelland, Maier & Neustadt, L.L.P.

(57) ABSTRACT

The present invention relates to a pharmaceutical composition, a food composition or a cosmetic composition, containing one or more kinds of a compound represented by the following formula (I')

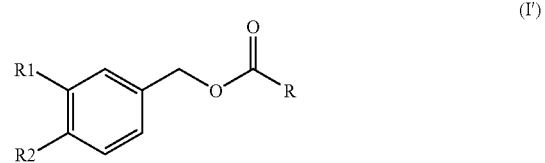

(I')

wherein R1 is a hydrogen atom, a hydroxyl group, a methoxy group or an ethoxy group, R2 is a hydroxyl group, a methoxy group or an acetoxy group, or R1 and R2 in combination optionally form a methylenedioxy group,
R is represented by the following formula

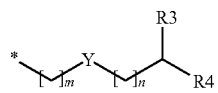

wherein Y is an ethylene group or a vinylene group, m and n are each an integer of 0 to 7, which satisfy m+n=2 to 8, and R3 and R4 are each independently a hydrogen atom, a methyl group or an ethyl group,
provided that,
(1) when R1 is a methoxy group, then R2 is not a hydroxyl group; and
(2) when R1 is a hydroxyl group, then R2 is not a hydroxyl group and an acetoxy group.
According to the present invention, a stable capsinoid derivative is provided, and a pharmaceutical composition, a food composition, a cosmetic composition and the like containing the derivative as an active ingredient can be provided.

56 Claims, No Drawings

SUBSTITUTED BENZYL ESTER DERIVATIVE AND USE THEREOF

CROSS-REFERENCE TO RELATED APPLICATIONS

The present application is a continuation of International patent application PCT/JP07/063170, filed on Jun. 29, 2007, which claims priority to Japanese patent application JP 2006-180433, filed on Jun. 29, 2006, which are incorporated herein by reference in their entireties.

TECHNICAL FIELD

The present invention relates to a novel substituted benzyl ester derivative, use thereof, and a production method thereof. More particularly, the present invention relates to a novel substituted benzyl ester derivative, a pharmaceutical composition, cosmetic, a food composition and the like, which comprise the derivative as an active ingredient.

BACKGROUND ART

Capsaicin which is a natural pungent component contained in planta (hereinafter capsicums) belonging to *Capsicum* is known to have a blood circulation enhancing action resulting from a peripheral vasodilatory action. However, capsaicin is problematic in that it causes strong irritation. On the other hand, capsinoids such as capsiate, dihydrocapsiate and the like have been reported as analogues of capsaicinoids such as capsaicin and the like. Since these capsinoids cause less pungent irritation as compared to capsaicinoids, they are expected to be usable for useful diet foods and the like (patent reference 1, non-patent reference 1).

In addition, vanillyl nonanoate, which is a capsinoid, is known to show a blood circulation enhancing action during external application (patent reference 2). However, capsinoids containing vanillyl nonanoate have vanillyl ester bond in molecule structure, and are not entirely sufficient in the stability (non-patent reference 2), and a component having high stability has been desired from the aspects of formulation of preparations and the like.

Although a case in which a substituted benzyl ester derivative was synthesized using various substituted benzyl alcohols instead of vanillyl alcohol and condensing with straight chain fatty acid is known (non-patent reference 2), TRPV1 (a capsaicin receptor) activating action or blood circulation enhancing action of these substituted benzyl ester derivatives has not been examined.

patent reference 1: JP-B-3345744
patent reference 2: WO2005/099682
non-patent reference 1: J. Agric. Food Chem., Vol. 46, No. 5 (1998), p. 1695-1697
non-patent reference 2: J. Agric. Food Chem., Vol. 49, No. 8 (2001), p. 4026-4030.

DISCLOSURE OF THE INVENTION

Problems to be Solved by the Invention

The present invention aims to provide a stable derivative of capsinoid and a composition comprising the derivative.

Means of Solving the Problems

The present inventors have conducted intensive studies in an attempt to solve the aforementioned problem and achieved stabilization while maintaining an ester structure, by converting a substituent on a benzene ring derived from vanillyl alcohol constituting capsinoids. In addition, they have found that some of such compounds are not only stable as compared to natural capsinoids but also show a blood circulation enhancing action, which resulted in the completion of the present invention.

Accordingly, the present invention includes the following.

[1] A compound represented by the following formula (I)

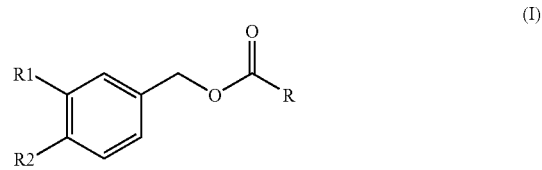

wherein R1 is a hydrogen atom, a hydroxyl group, a methoxy group or an ethoxy group, R2 is a hydroxyl group, a methoxy group or an acetoxy group, or R1 and R2 in combination optionally form a methylenedioxy group;
R is represented by the following formula

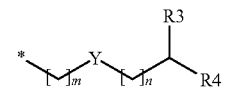

wherein Y is an ethylene group or a vinylene group, m and n are each an integer of 0 to 7, which satisfy m+n=2 to 8, and R3 and R4 are each independently a hydrogen atom, a methyl group or an ethyl group,
provided that,
(1) when R1 is a methoxy group, then R2 is not a hydroxyl group;
(2) when R1 is a hydroxyl group, then R2 is not a hydroxyl group and an acetoxy group;
(3) when R1 is a methoxy group and R2 is an acetoxy group, then R is not an n-octyl group;
(4) when R1 and R2 are methoxy groups, then R is not an n-octyl group;
(5) when R1 is a hydrogen atom and R2 is a hydroxyl group, then R is not an n-octyl group, an n-nonyl group and an n-undecyl group;
(6) when R1 is a hydrogen atom and R2 is a methoxy group, then R is not an n-pentyl group, an n-hexyl group, an n-nonyl group and an n-undecyl group; and
(7) when R1 and R2 in combination form a methylenedioxy group, then R is not an n-heptyl group and an n-undecyl group (hereinafter to be also referred to as compound (I)).

[2] The compound of the above-mentioned [1], wherein R1 and R2 in combination form a methylenedioxy group.
[3] The compound of the above-mentioned [1], wherein R1 is a methoxy group and R2 is an acetoxy group.
[4] The compound of the above-mentioned [1], wherein R1 and R2 are methoxy groups.
[5] The compound of the above-mentioned [1], wherein R1 is a hydrogen atom and R2 is a methoxy group.
[6] The compound of the above-mentioned [1], wherein R1 is a hydrogen atom and R2 is a hydroxyl group.
[7] The compound of the above-mentioned [1], wherein R1 is an ethoxy group and R2 is a hydroxyl group.
[8] The compound of the above-mentioned [1], wherein R1 is a hydroxyl group and R2 is a methoxy group.

[9] An external blood circulation enhancer comprising one or more kinds of a compound represented by the following formula (I')

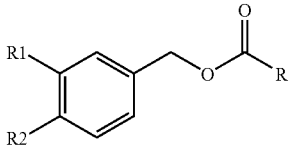

wherein R1 is a hydrogen atom, a hydroxyl group, a methoxy group or an ethoxy group, R2 is a hydroxyl group, a methoxy group or an acetoxy group, or R1 and R2 in combination optionally form a methylenedioxy group,
R is represented by the following formula

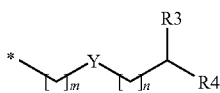

wherein Y is an ethylene group or a vinylene group, m and n are each an integer of 0 to 7, which satisfy m+n=2 to 8, and R3 and R4 are each independently a hydrogen atom, a methyl group or an ethyl group,
provided that (1) when R1 is a methoxy group, then R2 is not a hydroxyl group; and
(2) when R1 is a hydroxyl group, then R2 is not a hydroxyl group and an acetoxy group (hereinafter to be also referred to as compound (I')).
[10] A cosmetic composition comprising one or more kinds of compound (I').
[11] A food composition comprising one or more kinds of compound (I').
[12] The food composition of the above-mentioned [11], which is a sympathetic activation food.
[13] The food composition of the above-mentioned [11] or [12], which is a diet food.
[14] A method of producing compound (I'), comprising subjecting a benzyl alcohol derivative represented by the following formula (II')

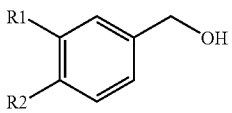

wherein R1 is a hydrogen atom, a hydroxyl group, a methoxy group or an ethoxy group, R2 is a hydroxyl group, a methoxy group or an acetoxy group, or R1 and R2 in combination optionally form a methylenedioxy group,
provided that (1) when R1 is a methoxy group, then R2 is not a hydroxyl group; and
(2) when R1 is a hydroxyl group, then R2 is not a hydroxyl group and an acetoxy group, and at least one selected from a fatty acid represented by the following formula (IIIa)

 HO₂C—R    (IIIa)

wherein R is a group represented by the following formula (III')

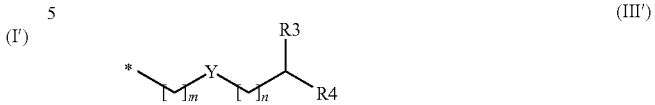

wherein Y is an ethylene group or a vinylene group, m and n are each an integer of 0 to 7, which satisfy m+n=2 to 8, and R3 and R4 are each independently a hydrogen atom, a methyl group or an ethyl group,
a fatty acid ester represented by the following formula (IIIb)

 R5-O₂C—R    (IIIb)

wherein R5 is an aliphatic hydrocarbon group and R is as defined above, and
a triglyceride represented by the following formula (IIIc)

wherein at least one of R6, R7 and R8 is a group represented by the above-mentioned formula (III') and the rest are each independently an aliphatic hydrocarbon group, to a dehydration condensation reaction in the presence of an enzyme catalyst.

Effect of the Invention

The present invention provides stable capsinoid analogs and consequently provides safe and promising pharmaceutical agents, cosmetics, diet foods and the like, which have a sympathetic activation action and a blood circulation enhancing action.

BEST MODE FOR CARRYING OUT THE INVENTION

The present invention is explained in detail in the following.

Examples of the aliphatic hydrocarbon group for R5 and the like include a straight chain or branched chain alkyl group having a carbon number of 1 to 6 (e.g., methyl, ethyl, n-propyl, isopropyl, n-butyl, isobutyl, sec-butyl, tert-butyl, n-pentyl, isopentyl, neopentyl, 1-ethylpropyl, n-hexyl, isohexyl, 1,1-dimethylbutyl, 2,2-dimethylbutyl, 3,3-dimethylbutyl etc.) or a straight chain or branched chain alkenyl group having a carbon number of 2 to 6 (e.g., vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl etc.) Among these, methyl, ethyl and vinyl are preferable.

The novel compound found by the present invention is a compound represented by the following formula (I).

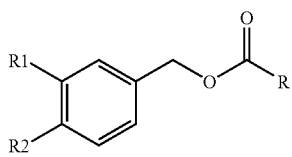

wherein R1 is a hydrogen atom, a hydroxyl group, a methoxy group or an ethoxy group, R2 is a hydroxyl group, a methoxy group or an acetoxy group, or R1 and R2 in combination optionally form a methylenedioxy group.

R is represented by the following formula

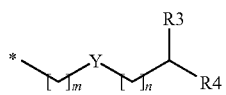

wherein Y is an ethylene group or a vinylene group, m and n are each an integer of 0 to 7, which satisfy m+n=2 to 8, and R3 and R4 are each independently a hydrogen atom, a methyl group or an ethyl group, provided that, (1) when R1 is a methoxy group, then R2 is not a hydroxyl group;

(2) when R1 is a hydroxyl group, then R2 is not a hydroxyl group and an acetoxy group;

(3) when R1 is a methoxy group and R2 is an acetoxy group, then R is not an n-octyl group;

(4) when R1 and R2 are methoxy groups, then R is not an n-octyl group;

(5) when R1 is a hydrogen atom and R2 is a hydroxyl group, then R is not an n-octyl group, an n-nonyl group and an n-undecyl group;

(6) when R1 is a hydrogen atom and R2 is a methoxy group, then R is not an n-pentyl group, an n-hexyl group, an n-nonyl group and an n-undecyl group; and (7) when R1 and R2 in combination form a methylenedioxy group, then R is not an n-heptyl group and an n-undecyl group.

Compound (I) characteristically has a chemical structure wherein a substituted benzyl alcohol derivative obtained by converting a substituent on a benzene ring of vanillyl alcohol (vanillyl alcohol, 4-hydroxy-3-methoxyvanillyl alcohol) and fatty acid are ester bonded.

However, the above-mentioned formula (I), wherein R1 is a methoxy group and R2 is a hydroxyl group, is a fatty acid ester of vanillyl alcohol, and is excluded by the above-mentioned proviso (1).

In addition, since the above-mentioned formula (I), wherein R1 is a hydroxyl group and R2 is a hydroxyl group or an acetoxy group, is problematic in the stability of a compound and the like, it is excluded by the above-mentioned proviso (2).

Furthermore, of the formula (I), embodiments defined by the following (a) to (e), such as 4-acetoxy-3-methoxybenzyl nonanoate represented by the following formula

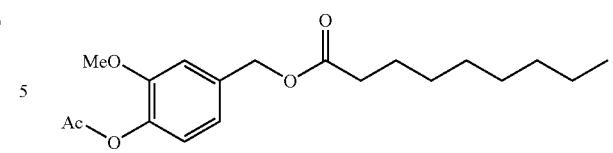

and the like are disclosed in known references (non-patent document 2 etc.)

(a) a compound wherein R1 is a methoxy group, R2 is an acetoxy group and R is an n-octyl group;

(b) a compound wherein R1 and R2 are methoxy groups and R is an n-octyl group;

(c) a compound wherein R1 is a hydrogen atom, R2 is a hydroxyl group and R is an n-octyl group, an n-nonyl group or an n-undecyl group;

(d) a compound wherein R1 is a hydrogen atom, R2 is a methoxy group and R is an n-pentyl group, an n-hexyl group, an n-nonyl group or an n-undecyl group;

(e) a compound wherein R1 and R2 in combination form a methylenedioxy group and R is an n-heptyl group or an n-undecyl group.

To avoid accidental coincidence, therefore, known compounds defined by the above-mentioned (a) to (e) such as 4-acetoxy-3-methoxybenzyl nonanoate are excluded by the above-mentioned provisos (3) to (7).

Preferable examples of compound (I) include a substituted benzyl ester derivative of branched chain fatty acid having a carbon number of 8 to 16, preferably 8 to 14, and a substituted benzyl ester of straight chain fatty acid having a carbon number of 4 to 15, preferably 8 to 13. However, known compounds are excluded from the substituted benzyl ester derivatives of straight chain fatty acid, as mentioned above.

More preferable specific examples of compound (I) include substituted benzyl fatty acid esters represented by the following formulas (Ia), (Ib), (Ic), (Id), (If), (Ig) and (Ih).

Fatty Acid Ester of Piperonyl Alcohol (Type A)

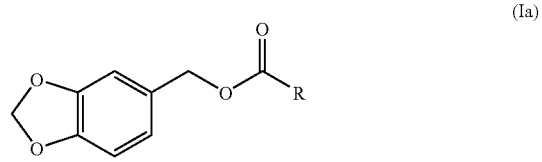

Fatty Acid Ester of Isovanillyl Alcohol (Type B)

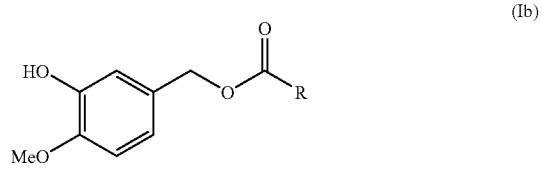

Fatty Acid Ester of p-Anisyl Alcohol (4-methoxybenzyl Alcohol) (Type C)

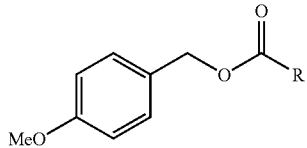
(Ic)

Fatty Acid Ester of Veratryl Alcohol (3,4-dimethoxybenzyl Alcohol) (Type D)

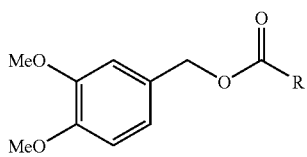
(Id)

Fatty Acid Ester of 4-hydroxybenzyl Alcohol (Type F)

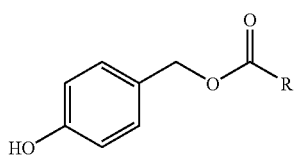
(If)

Fatty Acid Ester of 4-acetoxy-3-methoxybenzyl Alcohol (Type G)

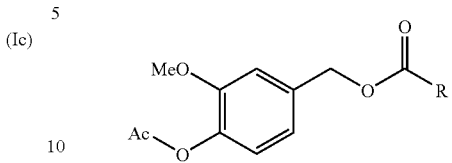
(Ig)

Fatty Acid Ester of 3-ethoxy-4-hydroxybenzyl Alcohol (Type H)

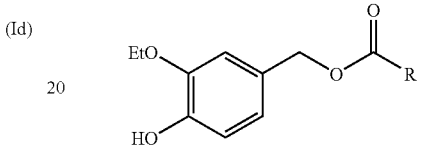
(Ih)

wherein R is as defined above.

The substituted benzyl fatty acid esters represented by the formulas (Ia), (Ib), (Ic), (If), (Ig) and (Ih) are preferable, and the substituted benzyl fatty acid esters represented by the formulas (Ib), (Ic), (Ig) and (Ih) are further preferable.

Of these, an ester form of saturated or unsaturated branched fatty acid, which is a partial structure of capsaicinoids contained in *Capsicum*, and substituted benzyl alcohol is preferable.

Preferable specific examples of the substituted benzyl ester derivative having a branched fatty acid side chain of capsaicinoids of the present invention are shown in the following Table 1.

TABLE 1

| substituted benzyl moiety | carboxylic acid moiety (R—COOH) | name of carboxylic acid moiety |
|---|---|---|
|  |  | 9-methyldecanoic acid |
|  |  | 8-methyldecanoic acid |
|  |  | 7-methylnonanoic acid |
|  |  | 7-methyloctanoic acid |

TABLE 1-continued

| substituted benzyl moiety | carboxylic acid moiety (R—COOH) | name of carboxylic acid moiety |
|---|---|---|
| HO-C6H4-CH2-O-C(=O)-R | (CH3CH2)CH(CH3)-CH2CH2CH2CH2-CO2H | 6-methyloctanoic acid |
| MeO, Ac-O-C6H3-CH2-O-C(=O)-R or | (CH3)2CH-CH2-CH2CH2CH2-CO2H | 6-methyl-4-heptanoic acid |
| EtO, HO-C6H3-CH2-O-C(=O)-R | (CH3)2CH-CH=CH-CH2-CO2H | (E)-6-methyl-4-heptenoic acid |
| | (CH3)2CH-CH=CH-CH2CH2-CO2H | (E)-7-methyl-5-octenoic acid |
| | (CH3)2CH-CH=CH-CH2CH2CH2-CO2H | (E)-8-methyl-6-nonenoic acid |
| | (CH3CH2)CH(CH3)-CH=CH-CH2CH2CH2-CO2H | (E)-8-methyl-6-decenoic acid |
| | (CH3)2CH-CH2-CH=CH-CH2CH2CH2-CO2H | (E)-9-methyl-6-decenoic acid |
| | (CH3)2CH-CH2-CH=CH-CH2CH2CH2CH2-CO2H | (E)-9-methyl-7-decenoic acid |
| | (CH3)2CH-CH2-CH=CH-(CH2)5-CO2H | (E)-10-methyl-8-undecenoic acid |
| | (CH3)2CH-CH2-CH=CH-(CH2)6-CO2H | (E)-11-methyl-9-dodecenoic acid |

A compound of the formula (I) wherein Y is an ethylene group or a vinylene group, m is 2 to 4, n is 0, R3 and R4 are methyl groups or one is a methyl group and the other is an ethyl group is preferable. Furthermore, a compound of the formula (I) wherein Y is an ethylene group or a vinylene group, m is 2 to 4, n is 0, R3 and R4 are methyl groups is preferable.

Of these, a 8-methylnonanoic acid-substituted benzyl ester derivative (a compound of the formula (I) wherein Y is an ethylene group, m is 4, n is 0, and R3 and R4 are methyl groups), and a (E)-8-methyl-6-nonenoic acid-substituted benzyl ester derivative (a compound of the formula (I) wherein Y is a vinylene group, m is 4, n is 0 and R3 and R4 are methyl groups), each of which is a substituted benzyl ester derivative having a fatty acid side chain moiety of capsaicin, dihydrocapsaicin, are preferable. Particularly, a 8-methylnonanoic acid-substituted benzyl ester derivative (a compound of the formula (I) wherein Y is an ethylene group, m is 4, n is 0 and R3 and R4 are methyl groups) is preferable.

Other embodiments of the present invention relates to an external blood circulation enhancer, cosmetic composition, pharmaceutical composition and food composition comprising one or more kinds of a compound represented by the following formula (I')

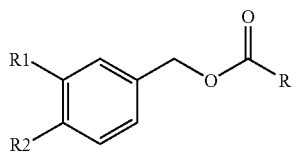

(I')

wherein R1 is a hydrogen atom, a hydroxyl group, a methoxy group or an ethoxy group, R2 is a hydroxyl group, a methoxy group or an acetoxy group, or R1 and R2 in combination optionally form a methylenedioxy group,
R is represented by the following formula

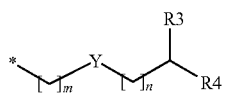

wherein Y is an ethylene group or a vinylene group, m and n are each an integer of 0 to 7, which satisfy m+n=2 to 8, and R3 and R4 are each independently a hydrogen atom, a methyl group or an ethyl group, provided that
(1) when R1 is a methoxy group, then R2 is not a hydroxyl group, and
(2) when R1 is a hydroxyl group, then R2 is not a hydroxyl group and an acetoxy group.

Compound (I') also includes, in addition to compound (I), known substituted benzyl ester derivatives defined by the above-mentioned (a) to (e), such as 4-acetoxy-3-methoxybenzyl nonanoate and the like. Specific examples, preferable embodiments and the like are the same as those for compound (I).

Here, when compound (I') is used as a component of a pharmaceutical agent, a food or cosmetics, only one kind of compound (I') may be added or a mixture of two or more kinds of compound (I') may be added.

Since compound (I') of the present invention has a blood circulation enhancing action also in external use, it is useful as an active ingredient of cosmetics. In addition, compound (I') of the present invention is assumed to have a capsaicin receptor-stimulating activity. Therefore, compound (I') of the present invention is considered to have, in addition to the aforementioned external blood circulation enhancing action, various physiological activities similar to those of capsaicinoids, such as sympathetic activation action, energy metabolism enhancing action, immunostimulatory action, lipolysis enhancing action, antiobesity action, body fat accumulation suppressive action, oral blood circulation enhancing action, analgesic action and the like. As such, compound of the present invention is considered to be also useful as an active ingredient of a pharmaceutical agent or a food additive.

Here, a capsaicin receptor is also called VR1 or Transient Receptor Potential Vanilloid Receptor 1 (TRPV1).

For measurement of the capsaicin receptor stimulating activity, for example, according to the following method, compound (I') of the present invention is brought into contact with a cell system that expresses TRPV1 and activation of TRPV1 is measured, whereby the sympathetic activation action of compound (I') of the present invention can be easily confirmed.

(1) Measurement of Capsaicin Receptor Stimulating Activity

A cell system that expresses TRPV1 can be obtained, for example, by transforming various cell lines such as *Xenopus* oocyte, chinese hamster ovary cell (CHO), baby hamster kidney (BHK) cell, human embryonic kidney (HEK) cell, Sf-9 insect cell, PC12 cell, CACO-2 cell and the like with a vector containing a gene encoding TRPV1 and the like (Michael J. Caterina, et al., Nature, 1997; 389, 816-824). In addition, when DNA encoding TRPV1 is to be incorporated into chromosome DNA to achieve permanent expression of TRPV1, the above-mentioned cells except *Xenopus* oocyte can be used. A DNA encoding TRPV1 can be introduced into these cells by a known method. The techniques necessary for the operations such as introduction of DNA encoding TRPV1 into the cell and the like are described in Sambrook, J., Fritsch, E. F., and Maniatis, T., "Molecular Cloning A Laboratory Manual, Second Edition", Cold Spring Harbor Laboratory Press, (1989) and the like.

TRPV1 may be a protein derived from mammals such as human, monkey, rat, mouse, dog, bovine, rabbit and the like, birds, fish or any other animal, and may be a variant thereof, as long as it accepts capsaicin or capsinoid and induces current change or membrane potential change, such as calcium, sodium and the like. The amino acid sequences of TRPV1 are registered under Accetion nos.: CAB89866 (human), NP_058903 (rat) in GenBank. In addition, the base sequences of a gene encoding TRPV1 are registered under Accetion nos.: AJ272063 (human), NM_017207 (rat) in GenBank. The base sequence encoding human TRPV1 is shown in SEQ ID NO: 1, and the amino acid sequence of human TRPV1 is shown in SEQ ID NO: 2.

The activation of TRPV1 can be measured, for example, by contacting compound (I') with a cell made to express TRPV1, and measuring the second messenger resulting from the binding of compound (I') to VR1, a membrane potential change and the like. The method of measuring the second messenger includes, for example, measurement of change of intracellular calcium concentration and the like. In addition, the activation of TRPV1 can also be measured by contacting compound (I') and TRPV1 against with a cell made to express TRPV1, measuring the membrane potential resulting from the binding of TRPV1 agonist to TRPV1, and measuring a membrane potential change due to the absence or presence of compound (I'). Here, the TRPV1 agonist also includes TRPV1 ligand.

Instead of detecting the second messenger, it is also possible to measure activation of TRPV1 by, using labeled known TRPV1 agonist, measuring the labeled agonist-TRPV1 binding, and detecting inhibition of the aforementioned binding by compound (I').

Examples of the TRPV1 agonist include capsaicin, olvanil, and capsinoid. Examples of the capsinoid include capsiate, dihydrocapsiate, nordihydrocapsiate and capsiate derivatives such as vanillyl decanoate, vanillyl nonanoate, vanillyl octanoate and the like, and fatty acid esters of vanillyl alcohol and various straight chain or branched chain fatty acids which have a fatty acid chain length similar to that of nordihydrocapsiate. Capsiate (4-hydroxy-3-methoxybenzyl (E)-8-methyl-6-nonenoate, hereinafter to be sometimes abbreviated as "CST"), dihydrocapsiate (4-hydroxy-3-methoxybenzyl 8-methylnonanoate, hereinafter to be sometimes abbreviated "DCT"), and nordihydrocapsiate (4-hydroxy-3-methoxybenzyl 7-methyl-octanoate, hereinafter to be sometimes abbreviated as "NDCT") respectively have the following chemical formulas.

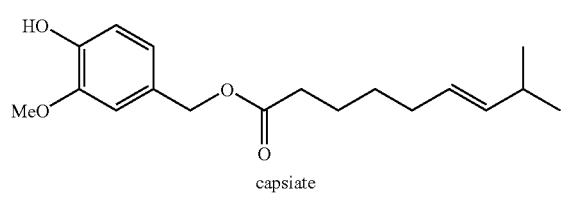

capsiate

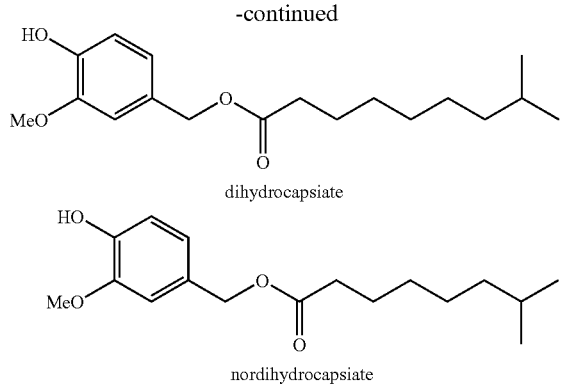

dihydrocapsiate nordihydrocapsiate

A pharmaceutical composition containing compound (I') of the present invention is particularly useful as a sympathetic activation agent, and can be used as various therapeutic agents such as an antiobesity agent, an immunostimulant, a blood circulation enhancer, an analgesic, an antipruritic and the like.

The form of the pharmaceutical composition of the present invention is not particularly limited, and any optional dosage form known in this technical field can be employed.

Examples thereof include oral preparation such as solid preparation, liquid agent and the like, parenteral preparations such as subcutaneous, intramuscular or intravenous injection, adhesive preparation, suppository, inhalant and the like. All of them can be produced according to methods known per se in this technical field.

Examples of the solid preparation include, but are not limited to, powder, granule, tablet, pill, capsule, troche, suppository and the like for oral administration, and examples of the liquid agent include, but are not limited to, solution, syrup, emulsion, suspension, inhalant and the like.

The content of compound (I') in the pharmaceutical composition is appropriately determined to achieve a suitable dose within the indicated range.

The pharmaceutical composition of the present invention can contain, where necessary, carrier, excipient, binder, swelling agent, flowability improving agent, lubricant, sweetening agent, flavor, preservative, antioxidant, coating agent, various vitamins, various amino acids and the like.

Specific examples of the components which can be contained in the pharmaceutical composition of the present invention include excipients such as microcrystalline cellulose, crystalline cellulose, lactose, corn starch, sucrose, glucose; binders such as tragacanth, gum arabic, corn starch, gelatin, polyvinyl alcohol, polyvinyl ether, ethylcellulose, methylcellulose, shellac, hydroxypropylcellulose, hydroxypropyl starch, polyvinylpyrrolidone; swelling agents such as corn starch, pregelatinated starch, alginic acid, dextrin; flowability improving agents such as fine silicon dioxide; lubricants such as glyceryl fatty acid ester, magnesium stearate, talc, polyethylene glycol, silica, hydrogenated vegetable oil; sweetening agents such as sucrose, lactose, aspartame, acesulfame-K, sucralose, monatin, stevia, saccharin and the like; flavors to be used for various foods such as peppermint, vanilla flavor, cherry, raspberry ketone and the like; preservatives such as paraoxybenzoates, chlorobutanol, benzyl alcohol, sorbic acid and the like, antioxidants such as sulfite, ascorbic acid, vitamin E, butylhydroxytoluene, sodium sulfite; coating agents such as shellac, sucrose, gelatin, hydroxypropylcellulose etc., and the like.

While the dose of compound of the present invention varies depending on the kind of disease, pathology, age and administration form, it is generally 0.01 mg to 20 g, preferably about 0.1 mg to 10 g, per day for an adult, which can be administered at once or in several portions.

The food composition of the present invention is useful as a sympathetic activation food, and is considered to particularly contribute to the promotion of fat burn by its sympathetic activation action. Thus, it can be preferably used as a food for diet purposes.

The "food" in the present invention refers to food in general, and includes, in addition to general foods including what is called health foods, such as food for specified health uses and food with nutrient function claims, which are defined in food with health claims system of the Ministry of Health, Labour and Welfare, and further includes dietary supplements.

The form of the food composition of the present invention is not particularly limited, and may be any as long as it permits oral ingestion.

Examples thereof include powder, granule, tablet, hard capsule, soft capsule, liquid (drinks, jelly drinks etc.), candy, chocolate and the like, all of which can be produced by a method known per se in this technical field.

The content of compound (I') in the food composition is appropriately determined to achieve a suitable dose within the indicated range.

Other food additives can be used as necessary for the food composition of the present invention. Examples of such food additive include fruit juice, dextrin, cyclic oligosaccharide, saccharides (monosaccharides such as fructose, glucose etc. and polysaccharides), acidulant, flavor, Matcha powder and the like for adjusting and improving taste, emulsifier, collagen, powdered milk, polysaccharide thickener, agar and the like for improving texture, and further, those generally used as components for general health foods and the like, such as vitamins, egg shell calcium, calcium pantothenate, other minerals, royal jelly, propolis, honey, dietary fibre, *Agaricus subrufescens*, chitin, chitosan, flavonoids, carotenoids, lutein, herbal medicine, chondroitin, various amino acids and the like.

The cosmetic composition of the present invention may concurrently contain conventionally-employed blood circulation enhancers where appropriate. Examples of such blood circulation enhancers include powdered *capsicum, capsicum* tincture, *capsicum* essence, capsaicin, homocapsaicin, homodihydrocapsaicin, vanillyl nonanamide and the like, capsaicin, ginger extract, *capsicum* extract, nicotinic acid, sophorae radix extract, *Astragalus* root extract, zingiber siccatum extract, safflower extract, Japanese pepper extract, Salvia miltiorrhiza extract, panacis japonici rhizoma extract, ginseng extract, γ-aminobutyric acid (GABA) and the like.

Furthermore, the cosmetic composition of the present invention may contain various components generally used as cosmetic or skin external preparations as long as the effect of the present invention is not inhibited. Examples of such components include oily base, surfactant, polymeric substance, solvent, powder substance, antioxidant, anti-inflammatory agent, UV absorber, skin-lightening agent, cellular stimulant, moisturizing agent, metal chelating agent, dyes, flavor, transdermal absorption enhancer and the like.

Examples of the oily base include hydrocarbons such as squalane, liquid paraffin, light liquid isoparaffin, heavy liquid isoparaffin, microcrystalline wax, solid paraffin and the like, silicones such as dimethicone, phenyldimethicone, cyclomethicone, amodimethicone, polyether-modified silicones and the like, esters such as jojoba oil, carnauba wax, *rhus suc-*

*cedanea* fruit wax, beeswax, whale wax, octyldodecyl oleate, isopropyl myristate, neopentylglycol diisostearate, diisostearyl malate and the like, fatty acids such as stearic acid, lauric acid, myristic acid, palmitic acid, isostearic acid, isopalmitic acid, behenic acid, oleic acid and the like, acylamino acids such as acyl glutamate, acylglycine, acylalanine, acylsarcosine and the like, higher alcohols such as behenyl alcohol, cetyl alcohol, oleyl alcohol, octadecyl alcohol and the like, triglycerides such as castor oil, coconut oil, hydrogenated coconut oil, camellia Japonica oil, wheatgerm oil, glycelyl triisostearate, glycelyl isooctanoate, olive oil etc., and the like.

Examples of the surfactant include nonionic surfactants such as sorbitan sesquioleate, sorbitan monooleate, sorbitan trioleate, sorbitan sesquistearate, sorbitan monostearate, sorbitan polyoxyethylene monooleate, sorbitan polyoxyethylene monostearate, polyoxyethylene stearate, polyoxyethylene oleate, polyoxyethylene glycerol fatty acid ester, polyoxyethylene alkylether, polyoxyethylene hydrogenated castor oil and the like, anionic surfactants such as sodium lauryl stearate, polyoxyethylenealkyl sulfate, sulfosuccinate salt, acylglutamate salt, acylsarcosinate salt, acylglycinate salt, acylalaninate salt and the like, cationic surfactants such as quaternary alkylammonium salt and the like, amphoteric surfactants such as alkylbetaine and the like, emulsifiers, solubilizers and the like.

Examples of the solvent include lower alcohols such as ethanol and the like, polyvalent alcohols such as 1,2-pentanediol, 1,2-hexylene glycol, isoprene glycol and the like, ethers and the other organic solvents, water and the like.

Examples of the polymeric substance include polyamino acids such as polyaspartic acid, ε-polylysine, γ-polyglutamic acid and the like and derivatives thereof, natural polymeric compounds such as collagen, elastin and the like, semisynthetic polymer compounds such as partially deacetylated chitin and the like, synthetic polymer compounds such as carboxymethylcellulose etc., and the like.

Examples of the powder substance include organic powders such as crystalline cellulose, crosslinking methylpolysiloxane, polyethylene powder, acrylic resin powder and the like, optionally surface-treated powders such as talc, mica, sericite, magnesium carbonate, calcium carbonate, titanium dioxide, iron oxide, iron blue, ultramarine blue, titanium mica, titanium sericite, silica and the like, pearlescent pigments such as hybrid fine powder, titanium dioxide-coated mica and the like, polymer powders such as photochromic pigment, nylon powder and the like, organic powders such as N-ε-lauroyllysine etc., and the like.

Examples of the dye include legal tar dye first category, legal tar dye second category, legal tar dye third category, hair dye, natural dye, mineral dye and the like.

Examples of the flavor include animal flavor such as musk and the like, plant flavors such as jasmine oil and the like, synthetic flavors such as α-amylcinnamaldehyde and the like, blended flavors and the like.

Examples of the transdermal absorption enhancer include urea, 2-pyrrolidone, 1-hexanol, 1-octanol, 1-decanol, 1-menthol, sodium lauryl sulfate, isopropyl myristate, n-hexyl acetate, oleic acid and the like.

The external blood circulation enhancer of the present invention can be used as cosmetics for skin and hair, bathwater additives or toiletry products by adding, where necessary, the aforementioned various other components according to a conventional method. The dosage form thereof is not particularly limited, and can take any dosage form such as solution state, paste state, gel state, solid state, powder state and the like. Examples thereof include oil, lotion, cream, emulsion, gel, shampoo, hair rinse, hair conditioner, enamel, foundation, lipstick, face powder, pack, ointment, granule, capsule, perfume, powder, cologne, toothpaste, soap, aerosol, cleansing foam and the like. Furthermore, the external blood circulation enhancer of the present invention can also be used for pharmaceutical agents or quasi-drugs for the prevention or improvement of various dermatic diseases, such as hair-growth medicine, an agent for antiaging and improving skin, skin essence, an agent for preventing and improving skin roughness due to capped skin•crack and the like.

While the content of compound of the present invention in cosmetic compositions also varies depending on the kind of component, it only needs to be contained at a level permitting provision of a desired blood circulation improving effect depending on the type of use, which is, for example, about 0.01 to 10 wt % of the cosmetic composition.

Compound (I') of the present invention can be produced by condensing substituted benzyl alcohol and fatty acid or a fatty acid ester thereof. A production method of compound (I') is explained in the following.

Production Method of Substituted Benzyl Alcohol Ester Compound (I')

A substituted benzyl alcohol ester compound represented by the formula (I') can be produced by (i) subjecting substituted benzyl alcohol (II') and fatty acid (IIIa) or a fatty acid ester thereof to a dehydration condensation reaction with an enzyme catalyst (lipase), (ii) subjecting substituted benzyl alcohol (II') and fatty acid (IIIa) to a chemical condensation reaction using a dehydration condensation agent, (iii) converting fatty acid (IIIa) to acid chloride and reacting acid chloride with substituted benzyl alcohol (II') in the presence of a base, and (iv) when a hydroxyl group is present on a benzene ring of ester derivative (I') obtained by any of (i) to (iii), acetylating, where necessary, the hydroxyl group by an enzymatic or chemical reaction.

The production method using an enzyme, particularly lipase, is explained in detail in the following, which is not to be construed as limitative.

Compound (I') can be produced by dehydration condensation of substituted benzyl alcohol (II') and a corresponding fatty acid (IIIa) and/or an ester form thereof by lipase in a solvent. The order of addition is not particularly limited.

The lipase to be used as the reaction catalyst may be any as long as it can catalyze this reaction, and lipases derived from microorganisms, animals or plants can be used without limitation. These lipases can be used alone or in a mixture thereof. From the aspects of re-use, such lipase is preferably immobilized by a conventional method to be used.

Particularly, lipase derived from microorganism is preferable. Specific examples include lipases derived from the genus *Candida* (e.g., *Candida antarctica, Candida cylindracea* etc.), the genus *Pseudomonas* (e.g., *Pseudomonas fluorescens, Pseudomonas* sp., *Pseudomonas cepacia* etc.), the genus *Alcaligenes* (e.g., *Alcaligenes* sp.), the genus *Aspergillus* (e.g., *Aspergillus niger* etc.), and the genus *Rhizopus* (e.g., *Rhizopus delemar, Rhizopus oryzae* etc.).

While these lipases are obtained by culturing the microorganisms producing them and the like, commercially available products can be preferably used. Examples of such commercially available lipases include immobilized enzymes such as Novozyme 435 (manufactured by Novozyme), Lipase AK (manufactured by Amano Pharmaceutical Co., Ltd.), Lipase PL (manufactured by Meito Sangyo Co., Ltd.), Lipase QL (manufactured by Meito Sangyo Co., Ltd.) and the like.

The amount of lipase to be used is generally 0.01- to 10-fold weight, generally preferably 0.05- to 5-fold weight, relative to substituted benzyl alcohol (II').

The fatty acid may be, in addition to fatty acid (IIIa) (free form), in the forms of various fatty acid derivatives such as fatty acid ester (IIIb), triglyceride (IIIc) and the like (hereinafter to be collectively abbreviated as fatty acid etc.).

The fatty acid etc. may be used alone or a combination of two or more kinds thereof may be used. When two or more kinds are used, the amounts thereof to be used can be converted based on the number of moles of substituent (IIIa') contained therein.

The amount of fatty acid etc. to be used may be 0.5- to 20-fold mol relative to substituted benzyl alcohol (II'), or the proportion of fatty acid etc. may be increased.

The solvent to be used is not particularly limited as long as it does not inhibit the reaction and, for example, ketone solvents such as acetone, 3-methyl-2-butanone, ethyl methyl ketone and the like; ether solvents such as dioxane, tetrahydrofuran, t-butyl methyl ether, diethyl ether and the like; nitrile solvents such as acetonitrile and the like; halogen solvents such as chloroform, methylene chloride and the like; hydrocarbon solvents such as hexane, heptane, toluene and the like; and the like can be mentioned. Among these, acetone and tetrahydrofuran are preferable. The amount of the solvent to be used is generally 50- to 500-fold weight, generally preferably 50- to 100-fold weight, relative to substituted benzyl alcohol (II').

To suppress hydrolysis of produced compound (I') by lipase, the solvent to be used is preferably subjected to a dehydrating treatment in advance with a dehydrating agent such as molecular sieve and the like.

In addition, when fatty acid (IIIa) is used, the reaction is preferably performed with the addition of a dehydrating agent, since water is produced with the progress of the reaction.

The amount of the dehydrating agent to be used is generally 10- to 100-fold weight, generally preferably 50- to 100-fold weight, relative to substituted benzyl alcohol (II').

The reaction time is preferably about 3 to 24 hr. This depends on the reaction temperature, whose range is 25° C. to 70° C.

While a method of dehydration condensation reaction of substituted benzyl alcohol (II') and fatty acid etc. by lipase using a solvent has been described above, the object substituted benzyl alcohol ester compound can be produced even without using a solvent. That is, when the reaction is performed under the above-mentioned reaction conditions without adding a solvent and a dehydrating agent, the resulting water is rapidly removed from the system, and substituted benzyl alcohol ester compound can be produced at a yield equivalent to or not less than the yield obtained using a solvent and a dehydrating agent. Furthermore, the reaction can be accelerated by removing generated water by reducing the pressure.

The obtained compound (I') can be isolated and purified according to a conventional method. For example, compound (I') can be isolated by separating and recovering lipase by filtration, salting out and the like, and then purified by extraction, concentration, crystallization, chromatography and the like.

EXAMPLES

While the usefulness of the present invention is concretely explained in the following by referring to Examples and Experimental Examples, it is not limited to these Examples. In the following Examples, the structures of synthesized compounds were identified by nuclear magnetic resonance spectrum (Bruker AVANCE400 (400 MHz)). GC-MS was performed using Hewlett-Packard Development Company, L.P., 5890SERIESII, 5972SERIES and 7673CONTROLLER.

Production Example 1

Synthesis of 8-methylnonanoic Acid

A 500 ml three-neck flask provided with a thermometer was purged with argon, and CuBr (481 mg, 3.36 mmol) was added. NMP (43.1 ml, 449 mmol) was added at room temperature and allowed to dissolve, and the reaction vessel was cooled to −20° C. THF (10 ml) was added thereto, and 6-bromo-n-hexanoic acid ethyl ester (25.0 g, 112 mmol) was added dropwise (inside temperature −8° C.). After stirring for 10 min, a solution (160 ml) of isobutylmagnesium bromide in THF prepared separately was slowly added dropwise over 60 min.

At 90 min from the completion of the dropwise addition, 10% aqueous ammonium chloride solution (120 ml) was slowly added dropwise to quench the reaction, and the mixture was extracted with n-hexane (120 ml). The n-hexane layer was washed with 10% aqueous ammonium chloride solution (100 ml), water (100 ml) and saturated brine (50 ml). The n-hexane layer was dried over anhydrous magnesium sulfate and filtered. The filtrate was concentrated under reduced pressure to give a crude product (24.2 g) of 8-methylnonanoic acid ethyl ester as a pale-yellow oil. The purity was measured by GC-MS and found to be 97.5%.

$^1$H-NMR (CDCl$_3$, δ): 0.860 (6H, d, J=6.63 Hz), 1.13-1.33 (11H, m), 1.48-1.64 (3H, m), 2.28 (2H, t, J=7.55 Hz), 4.12 (2H, q, J=7.13 Hz).

$^{13}$C-NMR (CDCl$_3$, δ): 14.60, 22.98, 25.36, 27.56, 28.30, 29.54, 29.89, 34.75, 39.31, 60.47, 174.2.

22.2 g from the obtained 8-methylnonanoic acid ethyl ester was placed in a 500 ml egg plant-shaped flask and dissolved in ethanol (77 ml). A 2M aqueous NaOH solution (77 ml, 154 mmol) was added dropwise at room temperature over 5 min. After the completion of the dropwise addition, the mixture was stirred with heating in an oil bath at 60° C. for 90 min. After confirmation of the disappearance of the starting materials by TLC, the mixture was cooled to room temperature.

Ethanol was concentrated under reduced pressure, and the residue was partitioned between water (40 ml) and t-butyl methyl ether (80 ml). The aqueous layer was further separated and washed twice with t-butyl methyl ether (80 ml). Then the aqueous layer was acidified by slowing adding 2M aqueous HCl solution (120 ml), and the mixture was extracted with n-hexane (80 ml). The n-hexane layer was washed with water (80 ml+40 ml) and saturated brine (40 ml), and the n-hexane layer was dried over anhydrous magnesium sulfate and filtered. The filtrate was concentrated under reduced pressure to give 17.3 g of 8-methylnonanoic acid as a pale-yellow oil. 15.3 g thereof was distilled under reduced pressure to give 12.7 g of 8-methylnonanoic acid as a pale-yellow oil. The purity was measured by GC-MS and found to be not less than 99.9%. Total yield from 6-bromo-n-hexanoic acid ethyl ester: 81%.

$^1$H-NMR (CDCl$_3$, δ): 0.862 (6H, d, J=6.64 Hz), 1.14-1.17 (2H, m), 1.26-1.35 (6H, m), 1.48-1.65 (3H, m), 2.35 (2H, t, J=7.52 Hz).

$^{13}$C-NMR (CDCl$_3$, δ): 22.95, 25.04, 27.55, 28.12, 29.47, 29.88, 34.51, 39.31, 181.0.

GC-MS: M=172.

Example 1

Synthesis of Piperonyl 8-methylnonanoate (Compound A)

Piperonyl alcohol (442 mg, 2.90 mmol), 8-methylnonanoic acid (500 mg, 2.90 mmol) and Novozyme 435 (50 mg) were measured and placed in a flask (25 ml). The mixture was stirred with heating in an oil bath at 50° C. for 16 hr without plugging the flask. After stirring with heating for 2 to 3 hr, attachment of water onto the upper wall of the flask was observed. The reaction mixture was allowed to cool to room temperature, hexane (25 ml) was added, and Novozyme 435 and the precipitated piperonyl alcohol were removed by filtration. Hexane (25 ml) was added to the filtrate, and the mixture was washed with 5% aqueous citric acid solution (25 ml×2) and saturated brine (25 ml) and dried over anhydrous magnesium sulfate. Magnesium sulfate was filtered off, and the filtrate was concentrated under reduced pressure. The residue was developed by PTLC (preparative thin layer chromatography, Merch Art. 13895) (n-hexane:ethyl acetate=4:1), and silica gel containing the object product was stirred with ethyl acetate (100 ml) for 30 min for extraction. The silica gel was filtered off, and the filtrate was concentrated under reduced pressure to give piperonyl 8-methylnonanoate (0.75 g, yield 84.3%) as a colorless oil.

$^1$H-NMR (DMSO-$d_6$, δ): 0.84 (6H, d, J=6.60 Hz), 1.05-1.15 (2H, m), 1.15-1.30 (6H, m), 1.42-1.60 (3H, m), 2.31 (2H, t, J=7.33 Hz), 4.97 (2H, s), 6.01 (2H, s), 6.82-6.92 (3H, m).

Example 1-1

Synthesis of Piperonyl 7-methyloctanoate (Compound A-1)

Using 7-methyloctanoic acid and in the same manner as in the aforementioned Example 1, the title compound was obtained as a colorless oil (yield 92.9%).

$^1$H-NMR (CDCl$_3$, δ): 0.85 (6H, d, J=6.64 Hz), 1.12-1.17 (2H, m), 1.26-1.30 (4H, m), 1.50 (1H, 7, J=6.64 Hz), 1.58-1.67 (2H, m), 2.33 (2H, t, J=7.56 Hz), 5.01 (2H, s), 5.96 (2H, s), 6.77-6.84 (3H, m).

Example 1-2

Synthesis of Piperonyl 6-methylheptanoate (Compound A-2)

Using 6-methylheptanoic acid and in the same manner as in the aforementioned Example 1, the title compound was obtained as a colorless oil (yield 91.6%).

$^1$H-NMR (CDCl$_3$, δ): 0.85 (6H, d, J=6.60 Hz), 1.13-1.19 (2H, m), 1.26-1.33 (2H, m), 1.51 (1H, 7, J=6.67 Hz), 1.59-1.65 (2H, m), 2.33 (2H, t, J=7.52 Hz), 5.01 (2H, s), 5.96 (2H, s), 6.77-6.84 (3H, m).

Example 2

Synthesis of Isovanillyl 8-methylnonanoate (Compound B)

Isovanillyl alcohol (447 mg, 2.90 mmol), 8-methylnonanoic acid (501 mg, 2.90 mmol) and Novozyme 435 (50 mg) were measured and placed in a flask (25 ml). The mixture was stirred with heating in an oil bath at 50° C. for 16 hr without plugging the flask. After stirring with heating for 2 to 3 hr, attachment of water onto the upper wall of the flask was observed. The reaction mixture was allowed to cool to room temperature, hexane (25 ml) was added, and Novozyme 435 and the insoluble material were removed by filtration. Hexane (25 ml) was added to the filtrate, and the mixture was washed with 5% aqueous citric acid solution (25 ml×2) and saturated brine (25 ml) and dried over anhydrous magnesium sulfate. Magnesium sulfate was filtered off, and the filtrate was concentrated under reduced pressure. The residue was developed by PTLC (n-hexane:ethyl acetate=2:1), and silica gel containing the object product was stirred with ethyl acetate (100 ml) for 30 min for extraction. The silica gel was filtered off, and the filtrate was concentrated under reduced pressure to give isovanillyl 8-methylnonanoate (0.72 g, yield 81.0%) as a colorless oil.

$^1$H-NMR (DMSO-$d_6$, δ): 0.84 (6H, d, J=6.60 Hz), 1.00-1.18 (2H, m), 1.18-1.30 (6H, m), 1.45-1.60 (3H, m), 2.30 (2H, t, J=7.36 Hz), 3.75 (3H, s), 4.93 (2H, s), 6.70-6.78 (2H, m), 6.87 (1H, d, J=8.16 Hz), 9.01 (1H, brs).

Example 2-1

Synthesis of Isovanillyl 7-Methyloctanoate (Compound B-1)

Using 7-methyloctanoic acid and in the same manner as in the aforementioned Example 2, the title compound was obtained as a colorless oil (yield 92.6%).

$^1$H-NMR (CDCl$_3$, δ): 0.86 (6H, t, J=3.32 Hz), 1.12-1.17 (2H, m), 1.24-1.30 (4H, m), 1.50 (1H, 7, J=6.64 Hz), 1.61-1.65 (2H, m), 2.33 (2H, t, J=7.58 Hz), 3.89 (3H, s), 5.01 (2H, s), 6.81-6.86 (2H, m), 6.94 (1H, d, J=1.72 Hz).

Example 2-2

Synthesis of Isovanillyl 7-methyl Nonanoate (Compound B-2)

Using 7-methylnonanoic acid in the same manner as in the aforementioned Example 2, the title compound was obtained as a colorless oil (yield 90.1%).

$^1$H-NMR (CDCl$_3$, δ): 0.84-0.87 (6H, m), 1.06-1.16 (2H, m), 1.26-1.36 (4H, m), 1.60-1.65 (2H, m), 2.33 (2H, t, J=7.58 Hz), 3.89 (3H, s), 5.01 (2H, s), 6.81-6.86 (2H, m), 6.94 (1H, d, J=2.12 Hz).

Example 3

Synthesis of 4-methoxybenzyl 8-methylnonanoate (Compound C)

4-Methoxybenzyl alcohol (603 mg, 4.35 mmol), 8-methylnonanoic acid (750 mg, 4.35 mmol) and Novozyme 435 (51 mg) were measured and placed in a flask (25 ml). The mixture was stirred with heating in an oil bath at 50° C. for 16 hr without plugging the flask. After stirring with heating for 2 to 3 hr, attachment of water onto the upper wall of the flask was observed. The reaction mixture was allowed to cool to room temperature, hexane (50 ml) was added, and Novozyme 435 and the insoluble material were removed by filtration. Hexane (25 ml) was added to the filtrate, and the mixture was washed with 5% aqueous citric acid solution (25 ml×2) and saturated brine (25 ml) and dried over anhydrous magnesium sulfate. Magnesium sulfate was filtered off, and the filtrate was concentrated under reduced pressure. The residue was developed by PTLC (n-hexane:ethyl acetate=3:1), and silica gel containing the object product was stirred with ethyl acetate (100 ml) for 30 min for extraction. The silica gel was filtered off, and the filtrate was concentrated under reduced pressure to give 4-methoxybenzyl 8-methylnonanoate (1.15 g, yield 90.2%) as a colorless oil.

$^1$H-NMR (DMSO-d$_6$, δ): 0.83 (6H, d, J=6.61 Hz), 1.08-1.18 (2H, m), 1.18-1.25 (6H, m), 1.40-1.55 (3H, m), 2.29 (2H, t, J=7.34 Hz), 3.75 (3H, s), 5.00 (2H, s), 6.91 (2H, d, J=8.70 Hz), 7.28 (2H, d, J=8.69 Hz).

Example 3-1

Synthesis of 4-methoxybenzyl 7-methyloctanoate (Compound C-1)

Using 7-methyloctanoic acid and in the same manner as in the aforementioned Example 3, the title compound was obtained as a colorless oil (yield 94.1%).

$^1$H-NMR (CDCl$_3$, δ): 0.85 (6H, d, J=6.64 Hz), 1.11-1.16 (2H, m), 1.25-1.29 (4H, m), 1.50 (1H, 7, J=6.63 Hz), 1.58-1.66 (2H, m), 2.32 (2H, t, J=7.56 Hz), 3.81 (3H, s), 5.04 (2H, s), 6.87-6.90 (2H, m), 7.27-7.31 (2H, m).

Example 3-2

Synthesis of 4-methoxybenzyl 6-methyloctanoate (Compound C-2)

Using 6-methyloctanoic acid and in the same manner as in the aforementioned Example 3, the title compound was obtained as a colorless oil (yield 96.5%).

$^1$H-NMR (CDCl$_3$, δ): 0.81-0.86 (6H, m), 1.07-1.14 (2H, m), 1.23-1.35 (5H, m), 1.57-1.65 (2H, m), 2.33 (2H, t, J=7.52 Hz), 3.81 (3H, s), 5.05 (2H, s), 6.87-6.90 (2H, m), 7.27-7.31 (2H, m).

Example 4

Synthesis of Veratryl 8-methylnonanoate (Compound D)

Veratryl alcohol (734 mg, 4.53 mmol), 8-methylnonanoic acid (751 mg, 4.35 mmol) and Novozyme 435 (51 mg) were measured and placed in a flask (25 ml). The mixture was stirred with heating in an oil bath at 50° C. for 16 hr without plugging the flask. After stirring with heating for 2 to 3 hr, attachment of water onto the upper wall of the flask was observed. The reaction mixture was allowed to cool to room temperature, hexane (50 ml) was added, and Novozyme 435 and the insoluble material were removed by filtration. Hexane (25 ml) was added to the filtrate, and the mixture was washed with 5% aqueous citric acid solution (25 ml×2) and saturated brine (25 ml) and dried over anhydrous magnesium sulfate. Magnesium sulfate was filtered off, and the filtrate was concentrated under reduced pressure. The residue was developed by PTLC (n-hexane:ethyl acetate=3:1), and silica gel containing the object product was stirred with ethyl acetate (100 ml) for 30 min for extraction. The silica gel was filtered off, and the filtrate was concentrated under reduced pressure to give veratryl 8-methylnonanoate (1.25 g, yield 89.1%) as a colorless oil.

$^1$H-NMR (CDCl$_3$, δ): 0.85 (6H, d, J=7.32 Hz), 1.10-1.20 (2H, m), 1.20-1.35 (6H, m), 1.45-1.55 (1H, m), 1.55-1.68 (2H, m), 2.35 (2H, t, J=7.44 Hz), 3.88 (3H, s), 5.05 (2H, s), 6.83-6.95 (3H, m).

Example 5

Synthesis of 4-hydroxybenzyl 8-methylnonanoate (Compound F)

4-Hydroxybenzyl alcohol (651 mg, 5.24 mmol), 8-methylnonanoic acid (948 mg, 5.50 mmol) and Novozyme 435 (50 mg) were measured and placed in a flask (25 ml). The mixture was stirred with heating in an oil bath at 50° C. for 16 hr without plugging the flask. After stirring with heating for 2 to 3 hr, attachment of water onto the upper wall of the flask was observed. The reaction mixture was allowed to cool to room temperature, hexane (50 ml) was added, and Novozyme 435 and the insoluble material were removed by filtration. Hexane (25 ml) was added to the filtrate, and the mixture was washed with 5% aqueous citric acid solution (25 ml×2) and saturated brine (25 ml) and dried over anhydrous magnesium sulfate. Magnesium sulfate was filtered off, and the filtrate was concentrated under reduced pressure to give 4-hydroxybenzyl 8-methylnonanoate (0.98 g, yield 67.3%) as a thin-yellow oil.

$^1$H-NMR (CDCl$_3$, δ): 0.86 (6H, d, J=6.61 Hz), 1.12-1.22 (2H, m), 1.24-1.38 (6H, m), 1.45-1.60 (1H, m), 1.60-1.70 (2H, m), 2.32 (2H, t, J=7.59 Hz), 5.04 (2H, s), 6.81 (2H, d, J=8.54 Hz), 7.23 (2H, d, J=8.54 Hz).

Example 6

Synthesis of 4-acetoxy-3-methoxybenzyl 8-methylnonanoate (1) (Compound G)

4-Acetoxy-3-methoxybenzyl alcohol (532 mg, 2.71 mmol) obtained by acetylating vanillin and reducing same with sodium borohydride and 8-methylnonanoic acid (491 mg, 2.85 mmol) were dissolved in methylene chloride (15 ml). The reaction mixture was maintained at 0° C., and WSC.HCl (1-ethyl-3-(3-dimethylaminopropyl)carbodiimide hydrochloride, (573 mg, 2.99 mmol) and DMAP (4-dimethylaminopyridine, 67 mg, 0.54 mmol) were added. The reaction mixture was stirred at 0° C. for 1 hr, allowed to gradually warm and stirred at room temperature for 16 hr. The reaction mixture was concentrated under reduced pressure and ethyl acetate (30 ml) was added to the residue. The reaction mixture was washed with water (20 ml), 5% aqueous citric acid solution (25 ml×2), saturated brine (20 ml), 5% aqueous sodium hydrogen carbonate solution (20 ml×2) and saturated brine (20 ml) and dried over anhydrous magnesium sulfate. Magnesium sulfate was filtered off, and the filtrate was concentrated under reduced pressure. The residue was developed by PTLC (n-hexane:ethyl acetate=4:1), and silica gel containing the object product was stirred with ethyl acetate (100 ml) for 30 min for extraction. The silica gel was filtered off, and the filtrate was concentrated under reduced pressure to give 4-acetoxy-3-methoxybenzyl 8-methylnonanoate (0.79 g, yield 89.9%) as a colorless oil.

$^1$H-NMR (CDCl$_3$, δ): 0.85 (6H, d, J=6.64 Hz), 1.10-1.20 (2H, m), 1.22-1.38 (6H, m), 1.48-1.57 (1H, m), 1.58-1.70 (2H, m), 2.31 (3H, s), 2.35 (2H, t, J=7.44 Hz), 3.84 (3H, s), 5.08 (2H, s), 6.92-7.02 (3H, m).

Example 7

Synthesis of 4-acetoxy-3-methoxybenzyl 8-methylnonanoate (2) (Compound G)

Vanillyl 8-methyl nonanoate (751 mg, 2.43 mmol) and acetic acid (0.146 ml, 2.55 mmol) were dissolved in methylene chloride (20 ml). The reaction mixture was maintained at 0° C., and WSC.HCl (490 mg, 2.55 mmol) and DMAP (60 mg, 0.49 mmol) were added. The reaction mixture was stirred at 0° C. for 1 hr, allowed to gradually warm and stirred at room temperature for 16 hr. The reaction mixture was concentrated under reduced pressure and ethyl acetate (30 ml) was added to the residue. The reaction mixture was washed with water (20 ml), 5% aqueous citric acid solution (25 ml×2), saturated brine (20 ml), 5% aqueous sodium hydrogen carbonate solution (20 ml×2) and saturated brine (20 ml) and dried over anhydrous magnesium sulfate. Magnesium sulfate was filtered off, and the filtrate was concentrated under reduced pressure. The residue was developed by PTLC (n-hexane:ethyl acetate=4:1), and silica gel containing the object product was stirred with ethyl acetate (100 ml) for 30 min for extraction. The silica gel was filtered off, and the filtrate was concentrated under reduced pressure to give 4-acetoxy-3-methoxybenzyl 8-methylnonanoate (0.73 g, yield 85.7%) as a colorless oil.

Example 7-1

Synthesis of 4-acetoxy-3-methoxybenzyl (E)-8-methyl-6-nonenoate (Compound G-1)

Using (E)-8-methyl-6-nonenoic acid and in the same manner as in the aforementioned Example 7, the title compound was obtained as a colorless oil (yield 83.1%).
$^1$H-NMR (CDCl$_3$, δ): 0.92-0.97 (6H, m), 1.38 (2H, 5, J=7.56 Hz), 1.63-1.69 (2H, m), 1.98 (2H, q, J=6.89 Hz), 2.22 (1H, 6, J=6.86 Hz), 2.31 (3H, s), 2.36 (2H, t, J=7.52 Hz), 3.84 (3H, s), 5.08 (2H, s), 5.28-5.41 (2H, m), 6.92-6.96 (2H, m), 7.01 (1H, d, J=7.96 Hz).

Example 8

Synthesis of 3-ethoxy-4-hydroxybenzyl 8-methylnonanoate (Compound H)

3-Ethoxy-4-hydroxybenzyl alcohol (733 mg, 4.35 mmol), 8-methylnonanoic acid (751 mg, 4.35 mmol) and Novozyme 435 (100 mg) were measured and placed in a flask (25 ml). The mixture was stirred with heating in an oil bath at 50° C. for 16 hr without plugging the flask. After stirring with heating for 2 to 3 hr, attachment of water onto the upper wall of the flask was observed. The reaction mixture was allowed to cool to room temperature, hexane (50 ml) was added, and Novozyme 435 and the insoluble material were removed by filtration. Hexane (25 ml) was added to the filtrate, and the mixture was washed with 5% aqueous citric acid solution (25 ml×2) and saturated brine (25 ml) and dried over anhydrous magnesium sulfate. Magnesium sulfate was filtered off, and the filtrate was concentrated under reduced pressure to give 3-ethoxy-4-hydroxybenzyl 8-methylnonanoate (1.25 g, yield 88.8%) as a colorless oil.
$^1$H-NMR (CDCl$_3$, δ): 0.86 (6H, d, J=6.61 Hz), 1.10-1.20 (2H, m), 1.20-1.35 (6H, m), 1.45 (3H, t, J=7.00 Hz), 1.45-1.55 (1H, m), 1.60-1.70 (2H, m), 2.32 (2H, t, J=7.64 Hz), 4.12 (2H, q, J=7.00 Hz), 5.02 (2H, s), 6.85-6.91 (3H, m).

Reference Example 1

Isolation and Purification of Vanillyl Decanoate by PTLC

Using vanillyl alcohol (1.70 g, 11.0 mmol) instead of piperonyl alcohol, and n-decanoic acid (1.72 g, 10 mmol) instead of 8-methylnonanoic acid in Example 1, a reaction similar to Example 1 was performed. The residue was purified by PTLC to find that the yield of the obtained vanillyl decanoate was 1.33 g (4.31 mmol, 43.1%), and vanillyl decanoate was decomposed by the contact with silica gel. In contrast, the isolation yield of piperonyl 8-methylnonanoate obtained by similar operation was 84.3% as in Example 1, suggesting that piperonyl 8-methylnonanoate is stabler than vanillyl decanoate even upon contact with silica gel.
$^1$H-NMR (CDCl$_3$, δ): 0.87 (t, 3H, J=7.1 Hz), 1.18-1.30 (m, 12H), 1.55-1.65 (m, 2H), 2.33 (t, 2H, J=7.7 Hz), 3.90 (s, 3H), 5.03 (s, 2H), 5.64 (br, 1H), 6.80-6.90 (m, 3H).

Using the yield (recovery rate) of purification by silica gel chromatography (PTLC) as an index, the stability of each Example compound was confirmed.

Isovanillyl 8-methylnonanoate (Compound B)

As shown in Example 2, the compound was not decomposed even after purification by PTLC, and isolated in a yield of 81.0%.

4-methoxybenzyl 8-methylnonanoate (Compound C)

As shown in Example 3, the compound was not decomposed even after purification by PTLC, and isolated in a yield of 90.2%.

Veratryl 8-methylnonanoate (Compound D)

As shown in Example 4, the compound was not decomposed even after purification by PTLC, and isolated in a yield of 89.1%.

4-acetoxy-3-methoxybenzyl 8-methylnonanoate (Compound G)

As shown in Examples 6 and 7, the compounds were not decomposed even after purification by PTLC, and isolated in a yield of 82.9% and 85.7%.

Experimental Example 1

Measurement of External Blood Circulation Enhancing Action

The compound of each Example and capsaicin analog were compared for vasodilatory effect using auricle of hairless mouse.
[Test method] A sample was applied to the right ear of hairless mouse (HR-1, female), and a control was applied to the left ear. Presence or absence of red spots development was visually evaluated, and evaluated according to the following indices.
○: clear red spots can be confirmed
Δ: weak red spots can be confirmed
x: no development of red spots
The samples were dissolved in liquid paraffin or ethanol.
samples:
(1) vanillyl alcohol (5 wt % solution in liquid paraffin or ethanol)
(2) capsaicin (1 wt % and 5 wt % solutions in liquid paraffin or ethanol)
(3) capsiate (1 wt % and 5 wt % solutions in liquid paraffin or ethanol)
(4) dihydrocapsiate (1 wt % and 5 wt % solutions in liquid paraffin)
(5) nordihydrocapsiate (1 wt % and 5 wt % solutions in liquid paraffin)
(6) compound A (5 wt % solution in liquid paraffin)

(7) compound A-1 (5 wt % solution in liquid paraffin or ethanol)
(8) compound A-2 (5 wt % solution in liquid paraffin or ethanol)
(9) compound B (5 wt % solution in liquid paraffin)
(10) compound B-1 (5 wt % solution in liquid paraffin)
(11) compound B-2 (5 wt % solution in liquid paraffin or ethanol)
(12) compound C (5 wt % solution in liquid paraffin)
(13) compound C-1 (5 wt % solution in liquid paraffin)
(14) compound C-2 (5 wt % solution in liquid paraffin)
(15) compound D (5 wt % solution in liquid paraffin)
(16) compound F (5 wt % solution in liquid paraffin)
(17) compound G (5 wt % solution in liquid paraffin)
(18) compound G-1 (5 wt % solution in liquid paraffin)
(19) compound H (5 wt % solution in liquid paraffin)
Control: liquid paraffin or ethanol The results of dissolution in liquid paraffin are shown in Table 2, and the results of dissolution in ethanol are shown in Table 3. Compound B, compound C, compound G and compound G-1 newly synthesized by the present inventors showed a strong vasodilating effect, and compound H showed a clear vasodilating effect, though the expression of the effect was slow. Compound A, compound B-1, compound C-1 and compound F showed a weak vasodilating effect. Compound A-1, compound A-2, compound C-2 and compound D did not show a vasodilating effect. Compound B-2 did not show a vasodilating effect when it was dissolved in liquid paraffin, but showed a vasodilating effect when it was dissolved in ethanol.

TABLE 2

Vasodilatory effect for hairless mouse - 1

| sample | 5 wt % (liquid paraffin) | 1 wt % (liquid paraffin) | note |
|---|---|---|---|
| vanillyl alcohol | x | — | no blood circulation enhancing effect |
| capsaicin | o | o | application of 1 wt %: red spots were observed even after lapse of 2 hr |
| capsiate | o | Δ | application of 5 wt %: weak red spots were observed even after lapse of 90 min |
| dihydro-capsiate | o | Δ | application of 5 wt %: weak red spots were observed even after lapse of 90 min |
| nordihydro-capsiate | o | Δ | application of 5 wt %: weak red spots were observed even after lapse of 90 min |
| compound A | Δ | — | vasodilatory effect started from about 30 min later and disappeard after lapse of 90 min |
| compound A-1 | x | — | no blood circulation enhancing effect |
| compound A-2 | x | — | no blood circulation enhancing effect |
| compound B | o | — | vasodilatory effect was observed even after lapse of 2 hr |
| compound B-1 | Δ | — | vasodilatory effect was confirmed 30 min later |

TABLE 2-continued

Vasodilatory effect for hairless mouse - 1

| sample | 5 wt % (liquid paraffin) | 1 wt % (liquid paraffin) | note |
|---|---|---|---|
| compound B-2 | x | — | vasodilatory effect was observed using 5 wt % ethanol |
| compound C | o | — | vasodilatory effect started from about 20 min later and observed even after lapse of 2 hr |
| compound C-1 | Δ | — | vasodilatory effect was observed immediately and disappeared 10 min later |
| compound C-2 | x | — | no blood circulation enhancing effect |
| compound D | x | — | no blood circulation enhancing effect |
| compound F | Δ | — | weak vasodilatory effect was observed for 60 min |
| compound G | o | — | vasodilatory effect was observed even after lapse of 90 min |
| compound G-1 | o | — | vasodilatory effect was observed 5 min later and disappeared 90 min later |
| compound H | o | — | vasodilatory effect started from about 30 min later and observed even after lapse of 2 hr |

TABLE 3

| sample | 5 wt % (ethanol) |
|---|---|
| vanillyl alcohol | x |
| capsaicin | o |
| capsiate | o |
| Compound A-1 | x |
| Compound A-2 | x |
| Compound B-2 | o |
| Compound C-2 | x |

INDUSTRIAL APPLICABILITY

Since the compound of the present invention has a sympathetic activation action, it is considered to contribute to fat-burning, and can be preferably used as a sympathetic activation agent (blood circulation enhancer), cosmetic, a material for diet food and the like.

This application is based on a patent application No. 2006-180433 filed in Japan, the contents of which are incorporated in full herein by this reference.

Although the present invention have been presented or described by referring to preferred embodiments of this invention, it will, however, be understood by those of ordinary skill in the art that various modifications may be made to the forms and details without departing from the scope of the invention as set forth in the appended claims. All patents, patent publications and other publications indicated or cited in the Specification are hereby incorporated in their entireties by reference.

The invention claimed is:

1. A compound represented by formula (I):

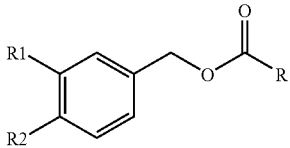

wherein R1 is a hydrogen atom, a hydroxyl group, a methoxy group or an ethoxy group, R2 is a hydroxyl group, a methoxy group or an acetoxy group, or R1 and R2 in combination optionally form a methylenedioxy group;
R is represented by the following formula

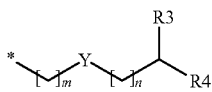

wherein Y is a vinylene group, m and n are each an integer of 0 to 7, which satisfy m+n=2 to 8, and R3 and R4 are each independently a hydrogen atom, a methyl group or an ethyl group,
provided that,
(1) when R1 is a methoxy group, then R2 is not a hydroxyl group; and
(2) when R1 is a hydroxyl group, then R2 is not a hydroxyl group or an acetoxy group.

2. The compound of claim 1, wherein R1 and R2 in combination form a methylenedioxy group.

3. The compound of claim 1, wherein R1 is a methoxy group and R2 is an acetoxy group.

4. The compound of claim 1, wherein R1 and R2 are methoxy groups.

5. The compound of claim 1, wherein R1 is a hydrogen atom and R2 is a methoxy group.

6. The compound of claim 1, wherein R1 is a hydrogen atom and R2 is a hydroxyl group.

7. The compound of claim 1, wherein R1 is an ethoxy group and R2 is a hydroxyl group.

8. The compound of claim 1, wherein R1 is a hydroxyl group and R2 is a methoxy group.

9. An external blood circulation enhancer, comprising one or more compounds according to claim 1.

10. A cosmetic composition, comprising one or more compounds according to claim 1.

11. A food composition, comprising one or more compounds according to claim 1.

12. The food composition of claim 11, which is a sympathetic activation food.

13. The food composition of claim 11, which is a diet food.

14. A method of producing a compound represented by formula (I'):

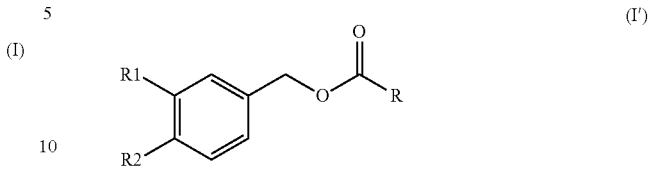

wherein R1 is a hydrogen atom, a hydroxyl group, a methoxy group or an ethoxy group, R2 is a hydroxyl group, a methoxy group or an acetoxy group, or R1 and R2 in combination optionally form a methylenedioxy group,
R is a group represented by formula (III'):

wherein Y is an ethylene group or a vinylene group, m and n are each an integer of 0 to 7, which satisfy m+n=2 to 8, and R3 and R4 are each independently a hydrogen atom, a methyl group or an ethyl group,
provided that,
(1) when R1 is a methoxy group, then R2 is not a hydroxyl group; and
(2) when R1 is a hydroxyl group, then R2 is not a hydroxyl group or an acetoxy group,
said method, comprising subjecting a benzyl alcohol compound represented by formula (II'):

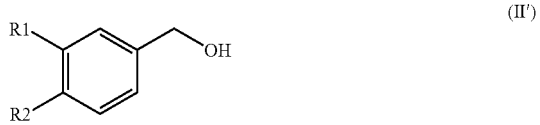

wherein each symbol is as defined above, and at least one compound selected from the group consisting of:
(a) a fatty acid represented by formula (IIIa):

wherein R is as defined above,
(b) a fatty acid ester represented by formula (IIIb):

wherein R5 is an aliphatic hydrocarbon group having a carbon number of 1 to 6 and R is as defined above, and
(c) a triglyceride represented by formula (IIIc):

wherein at least one of R6, R7 and R8 is a group represented by the above-mentioned formula (III') and the rest are each independently an aliphatic hydrocarbon group having a carbon number of 1 to 6, to a dehydration condensation reaction in the presence of a lipase.

15. The food composition of claim 12, which is a diet food.

16. A method for enhancing blood circulation, comprising administering an effective amount of a compound according to claim 1 to a subject in need thereof.

17. The method of claim 16, wherein R1 and R2 in combination form a methylenedioxy group.

18. The method of claim 16, wherein R1 is a methoxy group and R2 is an acetoxy group.

19. The method of claim 16, wherein R1 and R2 are methoxy groups.

20. The method of claim 16, wherein R1 is a hydrogen atom and R2 is a methoxy group.

21. A compound represented by formula (I):

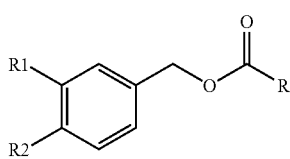
(I)

wherein R1 is a hydrogen atom, a hydroxyl group, a methoxy group or an ethoxy group, R2 is a hydroxyl group, a methoxy group or an acetoxy group, or R1 and R2 in combination optionally form a methylenedioxy group;
R is represented by the following formula

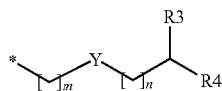

wherein Y is an ethylene group or a vinylene group, m and n are each an integer of 0 to 7, which satisfy m+n=2 to 8, and R3 and R4 are each independently a methyl group or an ethyl group,
provided that,
(1) when R1 is a methoxy group, then R2 is not a hydroxyl group; and
(2) when R1 is a hydroxyl group, then R2 is not a hydroxyl group or an acetoxy group.

22. The compound of claim 21, wherein R1 and R2 in combination form a methylenedioxy group.

23. The compound of claim 21, wherein R1 is a methoxy group and R2 is an acetoxy group.

24. The compound of claim 21, wherein R1 and R2 are methoxy groups.

25. The compound of claim 21, wherein R1 is a hydrogen atom and R2 is a methoxy group.

26. The compound of claim 21, wherein R1 is a hydrogen atom and R2 is a hydroxyl group.

27. The compound of claim 21, wherein R1 is an ethoxy group and R2 is a hydroxyl group.

28. The compound of claim 21, wherein R1 is a hydroxyl group and R2 is a methoxy group.

29. A cosmetic composition, comprising one or more compounds according to claim 21.

30. A food composition, comprising one or more compounds according to claim 21.

31. The food composition of claim 30, which is a sympathetic activation food.

32. The food composition of claim 30, which is a diet food.

33. The food composition of claim 31, which is a diet food.

34. A pharmaceutical composition, comprising at least one compound according to claim 21 and a pharmaceutically acceptable carrier.

35. A method for enhancing blood circulation, comprising administering an effective amount of a compound according to claim 21 to a subject in need thereof.

36. The method of claim 34, wherein R1 and R2 in combination form a methylenedioxy group.

37. The method of claim 34, wherein R1 is a methoxy group and R2 is an acetoxy group.

38. The method of claim 34, wherein R1 and R2 are methoxy groups.

39. The method of claim 34, wherein R1 is a hydrogen atom and R2 is a methoxy group.

40. A compound represented by formula (I):

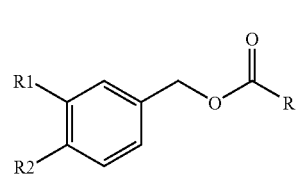
(I)

wherein R1 is a hydrogen atom, a hydroxyl group, a methoxy group or an ethoxy group, R2 is a hydroxyl group, a methoxy group or an acetoxy group;
R is represented by the following formula

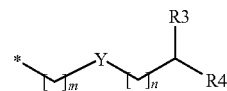

wherein Y is an ethylene group or a vinylene group, m and n are each an integer of 0 to 7, which satisfy m+n=2 to 8, and R3 and R4 are each independently a hydrogen atom, a methyl group or an ethyl group,
provided that,
(1) when R1 is a methoxy group, then R2 is not a hydroxyl group;
(2) when R1 is a hydroxyl group, then R2 is not a hydroxyl group or an acetoxy group;
(3) when R2 is an acetoxy group, then R is not an n-octyl group;
(4) when R1 and R2 are methoxy groups, then R is not an n-octyl group;
(5) when R1 is a hydrogen atom and R2 is a hydroxyl group, then R is not an n-octyl group, an n-nonyl group or an n-undecyl group; and
(6) when R1 is a hydrogen atom and R2 is a methoxy group, then R is not an n-pentyl group, an n-hexyl group, an n-nonyl group and an n-undecyl group.

41. The compound of claim 40, wherein R1 is a methoxy group and R2 is an acetoxy group.

42. The compound of claim 40, wherein R1 and R2 are methoxy groups.

43. The compound of claim 40, wherein R1 is a hydrogen atom and R2 is a methoxy group.

44. The compound of claim 40, wherein R1 is a hydrogen atom and R2 is a hydroxyl group.

45. The compound of claim 40, wherein R1 is an ethoxy group and R2 is a hydroxyl group.

46. The compound of claim 40, wherein R1 is a hydroxyl group and R2 is a methoxy group.

47. A cosmetic composition, comprising one or more compounds according to claim 40.

48. A food composition, comprising one or more compounds according to claim 40.

49. The food composition of claim 48, which is a sympathetic activation food.

50. The food composition of claim 48, which is a diet food.

51. The food composition of claim 49, which is a diet food.

52. A pharmaceutical composition, comprising at least one compound according to claim 40 and a pharmaceutically acceptable carrier.

53. A method for enhancing blood circulation, comprising administering an effective amount of a compound according to claim 40 to a subject in need thereof.

54. The method of claim 53, wherein R1 is a methoxy group and R2 is an acetoxy group.

55. The method of claim 53, wherein R1 and R2 are methoxy groups.

56. The method of claim 53, wherein R1 is a hydrogen atom and R2 is a methoxy group.

* * * * *

SEQUENCE LISTING

<160> NUMBER OF SEQ ID NOS: 2

<210> SEQ ID NO 1
<211> LENGTH: 2520
<212> TYPE: DNA

<213> ORGANISM: Homo sapiens
<220> FEATURE:
<221> NAME/KEY: CDS
<222> LOCATION: (1)..(2520)

<400> SEQUENCE: 1

```
atg aag aaa tgg agc agc aca gac ttg ggg gca gct gcg gac cca ctc        48
Met Lys Lys Trp Ser Ser Thr Asp Leu Gly Ala Ala Ala Asp Pro Leu
1               5                   10                  15 caa aag gac acc tgc cca gac ccc ctg gat gga gac cct aac tcc agg        96
Gln Lys Asp Thr Cys Pro Asp Pro Leu Asp Gly Asp Pro Asn Ser Arg
            20                  25                  30 cca cct cca gcc aag ccc cag ctc tcc acg gcc aag agc cgc acc cgg       144
Pro Pro Pro Ala Lys Pro Gln Leu Ser Thr Ala Lys Ser Arg Thr Arg
        35                  40                  45 ctc ttt ggg aag ggt gac tcg gag gag gct ttc ccg gtg gat tgc cct       192
Leu Phe Gly Lys Gly Asp Ser Glu Glu Ala Phe Pro Val Asp Cys Pro
    50                  55                  60 cac gag gaa ggt gag ctg gac tcc tgc ccg acc atc aca gtc agc cct       240
His Glu Glu Gly Glu Leu Asp Ser Cys Pro Thr Ile Thr Val Ser Pro
65                  70                  75                  80 gtt atc acc atc cag agg cca gga gac ggc ccc acc ggt gcc agg ctg       288
Val Ile Thr Ile Gln Arg Pro Gly Asp Gly Pro Thr Gly Ala Arg Leu
                85                  90                  95 ctg tcc cag gac tct gtc gcc gcc agc acc gag aag acc ctc agg ctc       336
Leu Ser Gln Asp Ser Val Ala Ala Ser Thr Glu Lys Thr Leu Arg Leu
            100                 105                 110 tat gat cgc agg agt atc ttt gaa gcc gtt gct cag aat aac tgc cag       384
Tyr Asp Arg Arg Ser Ile Phe Glu Ala Val Ala Gln Asn Asn Cys Gln
        115                 120                 125 gat ctg gag agc ctg ctg ctc ttc ctg cag aag agc aag aag cac ctc       432
Asp Leu Glu Ser Leu Leu Leu Phe Leu Gln Lys Ser Lys Lys His Leu
    130                 135                 140 aca gac aac gag ttc aaa gac cct gag aca ggg aag acc tgt ctg ctg       480
Thr Asp Asn Glu Phe Lys Asp Pro Glu Thr Gly Lys Thr Cys Leu Leu
145                 150                 155                 160 aaa gcc atg ctc aac ctg cac gac gga cag aac acc acc atc ccc ctg       528
Lys Ala Met Leu Asn Leu His Asp Gly Gln Asn Thr Thr Ile Pro Leu
                165                 170                 175 ctc ctg gag atc gcg cgg caa acg gac agc ctg aag gag ctt gtc aac       576
Leu Leu Glu Ile Ala Arg Gln Thr Asp Ser Leu Lys Glu Leu Val Asn
            180                 185                 190 gcc agc tac acg gac agc tac tac aag ggc cag aca gca ctg cac atc       624
Ala Ser Tyr Thr Asp Ser Tyr Tyr Lys Gly Gln Thr Ala Leu His Ile
        195                 200                 205 gcc atc gag aga cgc aac atg gcc ctg gtg acc ctg ctg gtg gag aac       672
Ala Ile Glu Arg Arg Asn Met Ala Leu Val Thr Leu Leu Val Glu Asn
    210                 215                 220 gga gca gac gtc cag gct gcg gcc cat ggg gac ttc ttt aag aaa acc       720
Gly Ala Asp Val Gln Ala Ala Ala His Gly Asp Phe Phe Lys Lys Thr
225                 230                 235                 240 aaa ggg cgg cct gga ttc tac ttc ggt gaa ctg ccc ctg tcc ctg gcc       768
Lys Gly Arg Pro Gly Phe Tyr Phe Gly Glu Leu Pro Leu Ser Leu Ala
                245                 250                 255 gcg tgc acc aac cag ctg ggc atc gtg aag ttc ctg ctg cag aac tcc       816
Ala Cys Thr Asn Gln Leu Gly Ile Val Lys Phe Leu Leu Gln Asn Ser
            260                 265                 270 tgg cag acg gcc gac atc agc gcc agg gac tcg gtg ggc aac acg gtg       864
Trp Gln Thr Ala Asp Ile Ser Ala Arg Asp Ser Val Gly Asn Thr Val
        275                 280                 285 ctg cac gcc ctg gtg gag gtg gcc gac aac acg gcc gac aac acg aag       912
```

```
                Leu His Ala Leu Val Glu Val Ala Asp Asn Thr Ala Asp Asn Thr Lys
                    290                 295                 300 ttt gtg acg agc atg tac aat gag att ctg atc ctg ggg gcc aaa ctg         960
Phe Val Thr Ser Met Tyr Asn Glu Ile Leu Ile Leu Gly Ala Lys Leu
305                 310                 315                 320 cac ccg acg ctg aag ctg gag gag ctc acc aac aag aag gga atg atg        1008
His Pro Thr Leu Lys Leu Glu Glu Leu Thr Asn Lys Lys Gly Met Met
                325                 330                 335 ccg ctg gct ctg gca gct ggg acc ggg aag atc ggg gtc ttg gcc tat        1056
Pro Leu Ala Leu Ala Ala Gly Thr Gly Lys Ile Gly Val Leu Ala Tyr
            340                 345                 350 att ctc cag cgg gag atc cag gag ccc gag tgc agg cac ctg tcc agg        1104
Ile Leu Gln Arg Glu Ile Gln Glu Pro Glu Cys Arg His Leu Ser Arg
        355                 360                 365 aag ttc acc gag tgg gcc tac ggg ccc gtg cac tcc tcg ctg tac gac        1152
Lys Phe Thr Glu Trp Ala Tyr Gly Pro Val His Ser Ser Leu Tyr Asp
    370                 375                 380 ctg tcc tgc atc gac acc tgc gag aag aac tcg gtg ctg gag gtg atc        1200
Leu Ser Cys Ile Asp Thr Cys Glu Lys Asn Ser Val Leu Glu Val Ile
385                 390                 395                 400 gcc tac agc agc agc gag acc cct aat cgc cac gac atg ctc ttg gtg        1248
Ala Tyr Ser Ser Ser Glu Thr Pro Asn Arg His Asp Met Leu Leu Val
                405                 410                 415 gag ccg ctg aac cga ctc ctg cag gac aag tgg gac aga ttc gtc aag        1296
Glu Pro Leu Asn Arg Leu Leu Gln Asp Lys Trp Asp Arg Phe Val Lys
            420                 425                 430 cgc atc ttc tac ttc aac ttc ctg gtc tac tgc ctg tac atg atc atc        1344
Arg Ile Phe Tyr Phe Asn Phe Leu Val Tyr Cys Leu Tyr Met Ile Ile
        435                 440                 445 ttc acc atg gct gcc tac tac agg ccc gtg gat ggc ttg cct ccc ttt        1392
Phe Thr Met Ala Ala Tyr Tyr Arg Pro Val Asp Gly Leu Pro Pro Phe
    450                 455                 460 aag atg gaa aaa act gga gac tat ttc cga gtt act gga gag atc ctg        1440
Lys Met Glu Lys Thr Gly Asp Tyr Phe Arg Val Thr Gly Glu Ile Leu
465                 470                 475                 480 tct gtg tta gga gga gtc tac ttc ttt ttc cga ggg att cag tat ttc        1488
Ser Val Leu Gly Gly Val Tyr Phe Phe Phe Arg Gly Ile Gln Tyr Phe
                485                 490                 495 ctg cag agg cgg ccg tcg atg aag acc ctg ttt gtg gac agc tac agt        1536
Leu Gln Arg Arg Pro Ser Met Lys Thr Leu Phe Val Asp Ser Tyr Ser
            500                 505                 510 gag atg ctt ttc ttt ctg cag tca ctg ttc atg ctg gcc acc gtg gtg        1584
Glu Met Leu Phe Phe Leu Gln Ser Leu Phe Met Leu Ala Thr Val Val
        515                 520                 525 ctg tac ttc agc cac ctc aag gag tat gtg gct tcc atg gta ttc tcc        1632
Leu Tyr Phe Ser His Leu Lys Glu Tyr Val Ala Ser Met Val Phe Ser
    530                 535                 540 ctg gcc ttg ggc tgg acc aac atg ctc tac tac acc cgc ggt ttc cag        1680
Leu Ala Leu Gly Trp Thr Asn Met Leu Tyr Tyr Thr Arg Gly Phe Gln
545                 550                 555                 560 cag atg ggc atc tat gcc gtc atg ata gag aag atg atc ctg aga gac        1728
Gln Met Gly Ile Tyr Ala Val Met Ile Glu Lys Met Ile Leu Arg Asp
                565                 570                 575 ctg tgc cgt ttc atg ttt gtc tac atc gtc ttc ttg ttc ggg ttt tcc        1776
Leu Cys Arg Phe Met Phe Val Tyr Ile Val Phe Leu Phe Gly Phe Ser
            580                 585                 590 aca gcg gtg gtg acg ctg att gaa gac ggg aag aat gac tcc ctg ccg        1824
Thr Ala Val Val Thr Leu Ile Glu Asp Gly Lys Asn Asp Ser Leu Pro
        595                 600                 605 tct gag tcc acg tcg cac agg tgg cgg ggg cct gcc tgc agg ccc ccc        1872
```

|     |     |     |     |     |     |     |     |     |     |     |     |      |
|-----|-----|-----|-----|-----|-----|-----|-----|-----|-----|-----|-----|------|
| Ser | Glu | Ser | Thr | Ser | His | Arg | Trp | Arg | Gly | Pro | Ala | Cys Arg Pro Pro |
|     | 610 |     |     |     | 615 |     |     |     | 620 |     |     |      |

```
gat agc tcc tac aac agc ctg tac tcc acc tgc ctg gag ctg ttc aag      1920
Asp Ser Ser Tyr Asn Ser Leu Tyr Ser Thr Cys Leu Glu Leu Phe Lys
625                 630                 635                 640 ttc acc atc ggc atg ggc gac ctg gag ttc act gag aac tat gac ttc      1968
Phe Thr Ile Gly Met Gly Asp Leu Glu Phe Thr Glu Asn Tyr Asp Phe
                645                 650                 655 aag gct gtc ttc atc atc ctg ctg gcc tat gta att ctc acc tac          2016
Lys Ala Val Phe Ile Ile Leu Leu Ala Tyr Val Ile Leu Thr Tyr
            660                 665                 670 atc ctc ctg ctc aac atg ctc atc gcc ctc atg ggt gag act gtc aac      2064
Ile Leu Leu Leu Asn Met Leu Ile Ala Leu Met Gly Glu Thr Val Asn
                675                 680                 685 aag atc gca cag gag agc aag aac atc tgg aag ctg cag aga gcc atc      2112
Lys Ile Ala Gln Glu Ser Lys Asn Ile Trp Lys Leu Gln Arg Ala Ile
                690                 695                 700 acc atc ctg gac acg gag aag agc ttc ctt aag tgc atg agg aag gcc      2160
Thr Ile Leu Asp Thr Glu Lys Ser Phe Leu Lys Cys Met Arg Lys Ala
705                 710                 715                 720 ttc cgc tca ggc aag ctg ctg cag gtg ggg tac aca cct gat ggc aag      2208
Phe Arg Ser Gly Lys Leu Leu Gln Val Gly Tyr Thr Pro Asp Gly Lys
                725                 730                 735 gac gac tac cgg tgg tgc ttc agg gtg gac gag gtg aac tgg acc acc      2256
Asp Asp Tyr Arg Trp Cys Phe Arg Val Asp Glu Val Asn Trp Thr Thr
                740                 745                 750 tgg aac acc aac gtg ggc atc atc aac gaa gac ccg ggc aac tgt gag      2304
Trp Asn Thr Asn Val Gly Ile Ile Asn Glu Asp Pro Gly Asn Cys Glu
                755                 760                 765 ggc gtc aag cgc acc ctg agc ttc tcc ctg cgg tca agc aga gtt tca      2352
Gly Val Lys Arg Thr Leu Ser Phe Ser Leu Arg Ser Ser Arg Val Ser
770                 775                 780 ggc aga cac tgg aag aac ttt gcc ctg gtc ccc ctt tta aga gag gca      2400
Gly Arg His Trp Lys Asn Phe Ala Leu Val Pro Leu Leu Arg Glu Ala
785                 790                 795                 800 agt gct cga gat agg cag tct gct cag ccc gag gaa gtt tat ctg cga      2448
Ser Ala Arg Asp Arg Gln Ser Ala Gln Pro Glu Glu Val Tyr Leu Arg
                805                 810                 815 cag ttt tca ggg tct ctg aag cca gag gac gct gag gtc ttc aag agt      2496
Gln Phe Ser Gly Ser Leu Lys Pro Glu Asp Ala Glu Val Phe Lys Ser
                820                 825                 830 cct gcc gct tcc ggg gag aag tga                                      2520
Pro Ala Ala Ser Gly Glu Lys
                835
```

<210> SEQ ID NO 2
<211> LENGTH: 839
<212> TYPE: PRT
<213> ORGANISM: Homo sapiens

<400> SEQUENCE: 2

```
Met Lys Lys Trp Ser Ser Thr Asp Leu Gly Ala Ala Ala Asp Pro Leu
1               5                   10                  15

Gln Lys Asp Thr Cys Pro Asp Pro Leu Asp Gly Asp Pro Asn Ser Arg
            20                  25                  30

Pro Pro Pro Ala Lys Pro Gln Leu Ser Thr Ala Lys Ser Arg Thr Arg
        35                  40                  45

Leu Phe Gly Lys Gly Asp Ser Glu Glu Ala Phe Pro Val Asp Cys Pro
    50                  55                  60

His Glu Glu Gly Glu Leu Asp Ser Cys Pro Thr Ile Thr Val Ser Pro
```

-continued

```
             65                  70                  75                  80
Val Ile Thr Ile Gln Arg Pro Gly Asp Gly Pro Thr Gly Ala Arg Leu
                     85                  90                  95
Leu Ser Gln Asp Ser Val Ala Ala Ser Thr Glu Lys Thr Leu Arg Leu
                    100                 105                 110
Tyr Asp Arg Arg Ser Ile Phe Glu Ala Val Ala Gln Asn Asn Cys Gln
                    115                 120                 125
Asp Leu Glu Ser Leu Leu Phe Leu Gln Lys Ser Lys Lys His Leu
                    130                 135                 140
Thr Asp Asn Glu Phe Lys Asp Pro Glu Thr Gly Lys Thr Cys Leu Leu
145                 150                 155                 160
Lys Ala Met Leu Asn Leu His Asp Gly Gln Asn Thr Thr Ile Pro Leu
                    165                 170                 175
Leu Leu Glu Ile Ala Arg Gln Thr Asp Ser Leu Lys Glu Leu Val Asn
                    180                 185                 190
Ala Ser Tyr Thr Asp Ser Tyr Tyr Lys Gly Gln Thr Ala Leu His Ile
                    195                 200                 205
Ala Ile Glu Arg Arg Asn Met Ala Leu Val Thr Leu Leu Val Glu Asn
                    210                 215                 220
Gly Ala Asp Val Gln Ala Ala Ala His Gly Asp Phe Phe Lys Lys Thr
225                 230                 235                 240
Lys Gly Arg Pro Gly Phe Tyr Phe Gly Glu Leu Pro Leu Ser Leu Ala
                    245                 250                 255
Ala Cys Thr Asn Gln Leu Gly Ile Val Lys Phe Leu Leu Gln Asn Ser
                    260                 265                 270
Trp Gln Thr Ala Asp Ile Ser Ala Arg Asp Ser Val Gly Asn Thr Val
                    275                 280                 285
Leu His Ala Leu Val Glu Val Ala Asp Asn Thr Ala Asp Asn Thr Lys
                    290                 295                 300
Phe Val Thr Ser Met Tyr Asn Glu Ile Leu Ile Leu Gly Ala Lys Leu
305                 310                 315                 320
His Pro Thr Leu Lys Leu Glu Glu Leu Thr Asn Lys Lys Gly Met Met
                    325                 330                 335
Pro Leu Ala Leu Ala Ala Gly Thr Gly Lys Ile Gly Val Leu Ala Tyr
                    340                 345                 350
Ile Leu Gln Arg Glu Ile Gln Glu Pro Glu Cys Arg His Leu Ser Arg
                    355                 360                 365
Lys Phe Thr Glu Trp Ala Tyr Gly Pro Val His Ser Ser Leu Tyr Asp
                    370                 375                 380
Leu Ser Cys Ile Asp Thr Cys Glu Lys Asn Ser Val Leu Glu Val Ile
385                 390                 395                 400
Ala Tyr Ser Ser Ser Glu Thr Pro Asn Arg His Asp Met Leu Leu Val
                    405                 410                 415
Glu Pro Leu Asn Arg Leu Leu Gln Asp Lys Trp Asp Arg Phe Val Lys
                    420                 425                 430
Arg Ile Phe Tyr Phe Asn Phe Leu Val Tyr Cys Leu Tyr Met Ile Ile
                    435                 440                 445
Phe Thr Met Ala Ala Tyr Tyr Arg Pro Val Asp Gly Leu Pro Pro Phe
450                 455                 460
Lys Met Glu Lys Thr Gly Asp Tyr Phe Arg Val Thr Gly Glu Ile Leu
465                 470                 475                 480
Ser Val Leu Gly Gly Val Tyr Phe Phe Arg Gly Ile Gln Tyr Phe
                    485                 490                 495
```

```
Leu Gln Arg Arg Pro Ser Met Lys Thr Leu Phe Val Asp Ser Tyr Ser
            500                 505                 510

Glu Met Leu Phe Phe Leu Gln Ser Leu Phe Met Leu Ala Thr Val Val
            515                 520                 525

Leu Tyr Phe Ser His Leu Lys Glu Tyr Val Ala Ser Met Val Phe Ser
            530                 535                 540

Leu Ala Leu Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
            565                 570                 575

Leu Cys Arg Phe Met Phe Val Tyr Ile Val Phe Leu Phe Gly Phe Ser
            580                 585                 590

Thr Ala Val Val Thr Leu Ile Glu Asp Gly Lys Asn Asp Ser Leu Pro
            595                 600                 605

Ser Glu Ser Thr Ser His Arg Trp Arg Gly Pro Ala Cys Arg Pro Pro
610                 615                 620

Asp Ser Ser Tyr Asn Ser Leu Tyr Ser Thr Cys Leu Glu Leu Phe Lys
625                 630                 635                 640

Phe Thr Ile Gly Met Gly Asp Leu Glu Phe Thr Glu Asn Tyr Asp Phe
            645                 650                 655

Lys Ala Val Phe Ile Ile Leu Leu Leu Ala Tyr Val Ile Leu Thr Tyr
            660                 665                 670

Ile Leu Leu Leu Asn Met Leu Ile Ala Leu Met Gly Glu Thr Val Asn
            675                 680                 685

Lys Ile Ala Gln Glu Ser Lys Asn Ile Trp Lys Leu Gln Arg Ala Ile
            690                 695                 700

Thr Ile Leu Asp Thr Glu Lys Ser Phe Leu Lys Cys Met Arg Lys Ala
705                 710                 715                 720

Phe Arg Ser Gly Lys Leu Leu Gln Val Gly Tyr Thr Pro Asp Gly Lys
            725                 730                 735

Asp Asp Tyr Arg Trp Cys Phe Arg Val Asp Glu Val Asn Trp Thr Thr
            740                 745                 750

Trp Asn Thr Asn Val Gly Ile Ile Asn Glu Asp Pro Gly Asn Cys Glu
            755                 760                 765

Gly Val Lys Arg Thr Leu Ser Phe Ser Leu Arg Ser Ser Arg Val Ser
            770                 775                 780

Gly Arg His Trp Lys Asn Phe Ala Leu Val Pro Leu Leu Arg Glu Ala
785                 790                 795                 800

Ser Ala Arg Asp Arg Gln Ser Ala Gln Pro Glu Glu Val Tyr Leu Arg
            805                 810                 815

Gln Phe Ser Gly Ser Leu Lys Pro Glu Asp Ala Glu Val Phe Lys Ser
            820                 825                 830

Pro Ala Ala Ser Gly Glu Lys
            835
```